United States Patent [19]
Mayer et al.

[11] Patent Number: 6,165,943
[45] Date of Patent: Dec. 26, 2000

[54] THIAZOLIMINE DERIVATIVES

[75] Inventors: Guido Mayer, Neustadt; Martina Otten, Ludwigshafen; Uwe Kardorff, Mannheim; Ernst Baumann, Dudenhofen; Wolfgang von Deyn, Neustadt; Stefan Engel, Idstein; Regina Luise Hill, Speyer; Joachim Rheinheimer; Matthias Witschel, both of Ludwigshafen; Roland Götz, Rothenburg; Michael Rack, Heidelberg; Karl-Otto Westphalen, Speyer; Ulf Misslitz, Neustadt; Helmut Walter, Obrigheim, all of Germany

[73] Assignee: BASF Aktiengesellschaft, Ludwigshafen, Germany

[21] Appl. No.: 09/381,463

[22] PCT Filed: Mar. 12, 1998

[86] PCT No.: PCT/EP98/01442

§ 371 Date: Sep. 21, 1999

§ 102(e) Date: Sep. 21, 1999

[87] PCT Pub. No.: WO98/42703

PCT Pub. Date: Oct. 1, 1998

[30] Foreign Application Priority Data

Mar. 24, 1997 [DE] Germany .......................... 197 12 226

[51] Int. Cl.⁷ ........................ C07D 417/04; A01N 43/78

[52] U.S. Cl. .................... 504/266; 548/193; 548/195; 548/196

[58] Field of Search ............................ 548/195, 196, 548/193; 504/266

[56] References Cited

FOREIGN PATENT DOCUMENTS

98/42703  10/1998  WIPO .................... 548/193

Primary Examiner—Robert Gerstl
Attorney, Agent, or Firm—Keil & Weinkauf

[57] ABSTRACT

Thiazolimine derivatives of the formula I

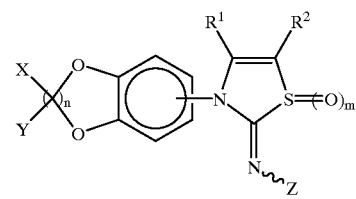

where:

X and Y independently of one another are each hydrogen, halogen, $C_1$–$C_4$-alkyl, $C_1$–$C_4$-haloalkyl;

Z is hydrogen; $C_1$–$C_8$-alkyl, $C_2$–$C_8$-alkenyl, $C_2$–$C_8$-alkynyl, $C_1$–$C_8$-alkoxy, $C_1$–$C_8$-alkylthio, it being possible for these groups to be substituted by one to five halogen or $C_1$–$C_4$-alkoxy; aryl, hetaryl, benzyl, it being possible for these groups to be substituted by $C_1$–$C_4$-alkyl, $C_1$–$C_4$-alkoxy, $C_1$–$C_4$-haloalkyl, $C_1$–$C_4$-haloalkoxy, halogen, nitro or cyano; or one of the groups below:

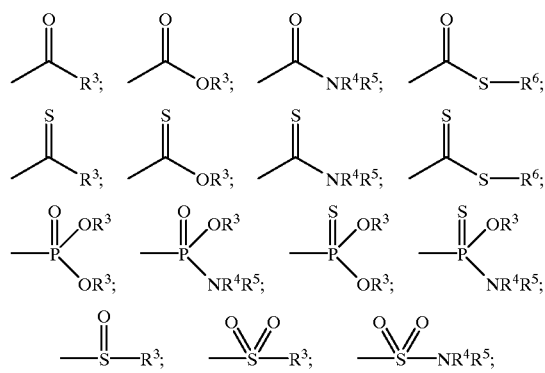

$R^1$ and $R^2$ are each hydrogen, halogen; $C_1$–$C_4$-alkyl, $C_2$–$C_4$-alkenyl, $C_2$–$C_4$-alkynyl, it being possible for these groups to be substituted by one to five halogens or by $C_1$–$C_4$-alkoxy;

n is 1 or 2;

m is 0, 1 or 2

$R^3$–$R^6$ are each as defined in the application, and agriculturally useful salts of the compounds I.

11 Claims, No Drawings

THIAZOLIMINE DERIVATIVES

This application is a 371 of PCT/EP98/01442 filed Mar. 12, 1998.

The present invention relates to novel thiazolimine derivatives having herbicidal activity, to a process for preparing the thiazolimine derivatives, to compositions comprising them and to the use of these derivatives or of the compositions comprising them for controlling weeds.

Herbicidally active thiazolimine derivatives are known from the literature (U.S. Pat. No. 5,244,863; EP 529 482, EP 446 802).

However, the herbicidal properties of the known compounds and their tolerability are not entirely satisfactory.

It is an object of the present invention to provide novel thiazolimine derivatives having improved properties.

We have found that this object is achieved by the novel thiazolimine derivatives of the formula I,

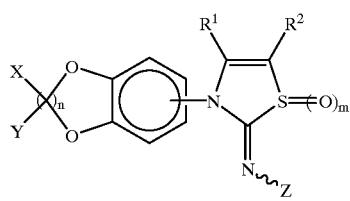

where:

X and Y independently of one another are each hydrogen, halogen, $C_1$–$C_4$-alkyl, $C_1$–$C_4$-haloalkyl;

Z is hydrogen; $C_1$–$C_8$-alkyl, $C_2$–$C_8$-alkenyl, $C_2$–$C_8$-alkynyl, $C_1$–$C_8$-alkoxy, $C_1$–$C_8$-alkylthio, it being possible for these groups to be substituted by one to five halogens or $C_1$–$C_4$-alkoxy; aryl, hetaryl, benzyl, it being possible for these groups to be substituted by $C_1$–$C_4$-alkyl, $C_1$–$C_4$-alkoxy, $C_1$–$C_4$-haloalkyl, $C_1$–$C_4$-haloalkoxy, halogen, nitro or cyano; or one of the groups below:

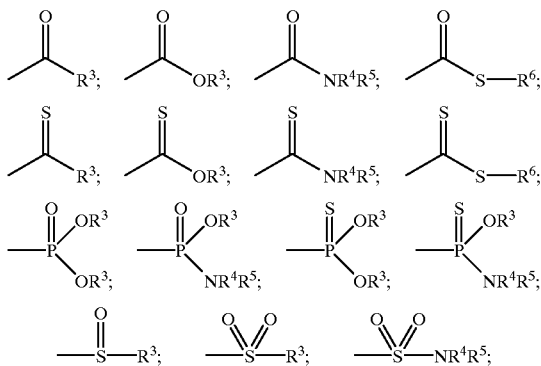

$R^1$ and $R^2$ are each hydrogen, halogen; $C_1$–$C_4$-alkyl, $C_2$–$C_4$-alkenyl, $C_2$–$C_4$-alkynyl, it being possible for these groups to be substituted by one to five halogens or by $C_1$–$C_4$-alkoxy;

$R^3$ is hydrogen; $C_1$–$C_8$-alkyl, $C_2$–$C_8$-alkenyl, $C_2$–$C_8$-alkynyl, $C_2$–$C_8$-alkylcarbonyl, $C_3$–$C_8$-alkenylcarbonyl, $C_3$–$C_8$-alkynylcarbonyl, it being possible for these groups to be substituted by one to eight halogens or by $C_1$–$C_4$-alkoxy; $C_3$–$C_7$-cycloalkyl, $C_3$–$C_7$-cycloalkenyl, it being possible for these groups to be substituted by one to eight halogen atoms, $C_1$–$C_4$-alkoxy, $C_1$–$C_4$-alkyl or $C_1$–$C_4$-haloalkyl; aryl, hetaryl, benzyl, it being possible for these groups to be substituted by $C_1$–$C_4$-alkyl, $C_1$–$C_4$-haloalkyl, $C_1$–$C_4$-alkoxy, $C_1$–$C_4$-haloalkoxy, halogen, cyano, or nitro;

$R^4$ and $R^5$ are each hydrogen; $C_1$–$C_6$-alkyl, $C_2$–$C_6$-alkenyl, $C_2$–$C_6$-alkynyl, it being possible for these groups to be substituted by one to four halogens or by $C_1$–$C_4$-alkoxy; $C_3$–$C_7$-cycloalkyl, $C_3$–$C_7$-cycloalkenyl, which may be substituted by one to four halogens or by $C_1$–$C_4$-alkyl, $C_1$–$C_4$-haloalkyl, $C_1$–$C_4$-alkoxy, $C_1$–$C_4$-haloalkoxy; aryl, hetaryl, it being possible for these groups to be substituted by $C_1$–$C_4$-alkyl, $C_1$–$C_4$-alkoxy, $C_1$–$C_4$-haloalkyl, $C_1$–$C_4$-haloalkoxy, halogen, nitro or cyano;

$R^4$ and $R^5$ together form a 3- to 7-membered heterocycle which may carry a further hetero atom from the group consisting of N, O and S, may contain at least one double bond and may be substituted by $C_1$–$C_4$-alkyl, $C_1$–$C_4$-haloalkyl, $C_1$–$C_4$-alkoxy, $C_1$–$C_4$-haloalkoxy, halogen, nitro or cyano;

$R^6$ is hydrogen; $C_1$–$C_6$-alkyl, $C_2$–$C_6$-alkenyl, $C_2$–$C_6$-alkynyl, it being possible for these groups to be substituted by one to four halogens or by alkoxy; $C_3$–$C_7$-cycloalkyl, $C_3$–$C_7$-cycloalkenyl, which may be substituted by one to four halogen atoms or by $C_1$–$C_4$-alkyl, $C_1$–$C_4$-haloalkyl, $C_1$–$C_4$-alkoxy, haloalkoxy; aryl, hetaryl, it being possible for these groups to be substituted by $C_1$–$C_4$-alkyl $C_1$–$C_4$-haloalkyl, $C_1$–$C_4$-alkoxy, $C_1$–$C_4$-haloalkoxy, halogen, nitro or cyano;

n is 1 or 2;

m is 0, 1 or 2 and agriculturally useful salts of the compounds I.

The thiazolimine derivatives of the formula I are prepared by reacting anilines of the formula II, which are known from DE 41 33 156, in the presence of an organic or inorganic base in a ratio of 0.5 to 5 equivalents with substituted propargyl derivatives of the general formula III in an inert solvent at from 0 to 100° C.

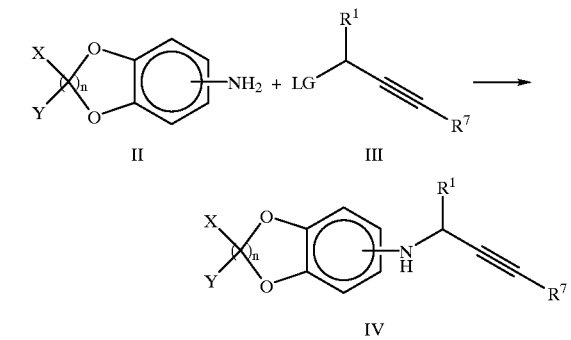

LG (leaving group) is a nucleophilically replaceable leaving group such as, for example, halogen, mesylate, tosylate or acetate.

In general, the reaction is carried out by adding the alkylating agent to the aniline derivative of the general formula II and the base. Suitable bases are tertiary amines, pyridine, the aniline derivative of the general formula II or potassium carbonate and cesium carbonate which are employed in a range of from 0.5 to 5 molar equivalents.

Suitable solvents are, for example, methylene chloride, chloroform, dioxan, tetrahydrofuran, dimethylformamide, acetonitrile, toluene or ethyl acetate.

During the addition of the alkylating agent of the general formula III, the reaction mixture is preferably stirred at a temperature from 0 to 150° C.

Work-up is carried out in a conventional manner; for example, the reaction mixture is poured into water and the product of value is extracted, for example, with methylene chloride. Further purification may be carried out, for example, by chromatography, crystallization or distillation. (Organikum, 16th Edition, VEB Deutscher Verlag der Wissenschaften, Berlin 1986; J. Fluorine Chem. 60, (1993), 31–38).

Compounds of the general formula VIII

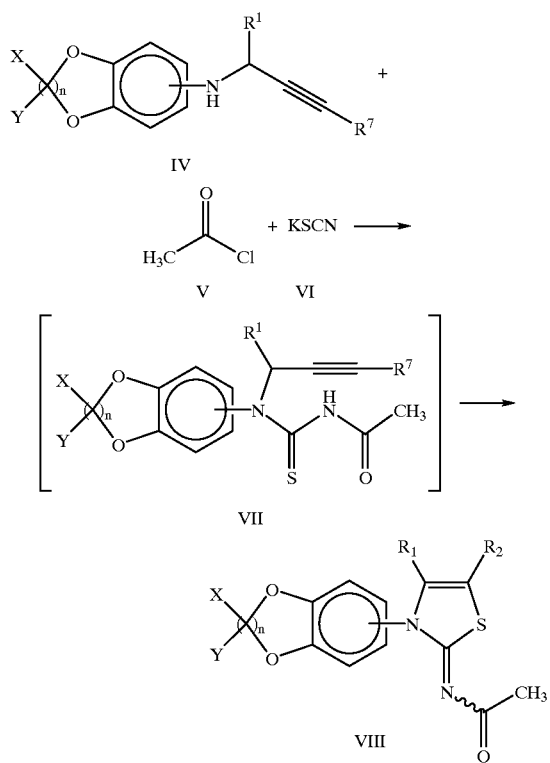

are prepared by reacting aniline derivatives of the general formula IV with a mixture of KSCN and acetyl chloride. The resulting product mixtures are then converted into the N-acetylthiazolimine derivatives VIII by treatment with acid or base (EP 446 820).

The reaction is generally carried out by adding the aniline derivative of the general formula IV to a reaction mixture of KSCN and acetyl chloride in an inert solvent such as, for example, methylene chloride, chloroform, dioxan, tetrahydrofuran, dimethylformamide, acetonitrile, toluene or ethyl acetate. During the entire reaction, the reaction mixture is preferably stirred at from −15° C. to 150° C.

Work-up is carried out in a customary manner; for example, the reaction mixture is poured onto water and the product of value is separated off by extraction with, for example, methylene chloride.

Further reaction is carried out after drying.

For this purpose, the reaction mixture is reacted either dissolved in an inert solvent, such as methylene chloride, chloroform, tetrahydrofuran or ethyl acetate, or else undiluted using an auxiliary reagent. The temperature is in the range from −15° C. to 150° C. The catalyst may be an inorganic acid, such as sulfuric acid, hydrochloric acid or phosphoric acid, an organic acid, such as acetic acid, trifluoroacetic acid or toluenesulfonic acid, or a base, such as potassium tert-butoxide, sodium methoxide, pyridine, triethylamine or dimethylaminopyridine. Work-up is carried out in a customary manner, for example by pouring the reaction mixture into water and separating off the product of value by extraction with, for example, methylene chloride. Purification may be carried out by crystallization or chromatography (EP 446 802).

To prepare compounds of the general formula IX, N-acetylthiazolimines of the general formula VIII are converted into their salts by acid hydrolysis.

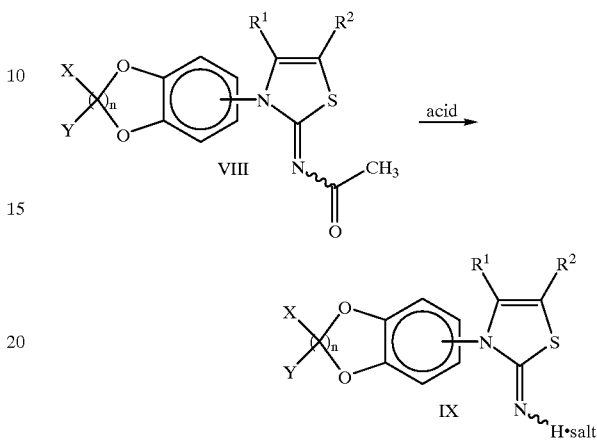

In general, the N-acetylthiazolimines of the general formula VIII are dissolved in an inert organic solvent, such as methylene chloride, chloroform, tetrahydrofuran, dimethylformamide, toluene, diethyl ether, methanol or ethanol, and reacted with from 1 to 100 equivalents of an organic or an inorganic acid. The temperature is usually from 0 to 150° C. Suitable acids are organic and inorganic acids, such as acetic acid, trifluoroacetic acid, p-toluenesulfonic acid or sulfuric acid, hydrochloric acid and phosphoric acid.

Work-up is generally carried out by removing the solvent under reduced pressure and purifying the remaining salt by crystallization from an inert solvent (T. W. Greene, Protective Groups in Organic Synthesis, Wiley, Interscience, N.Y.).

Compounds of the general formula I are prepared in the following manner:

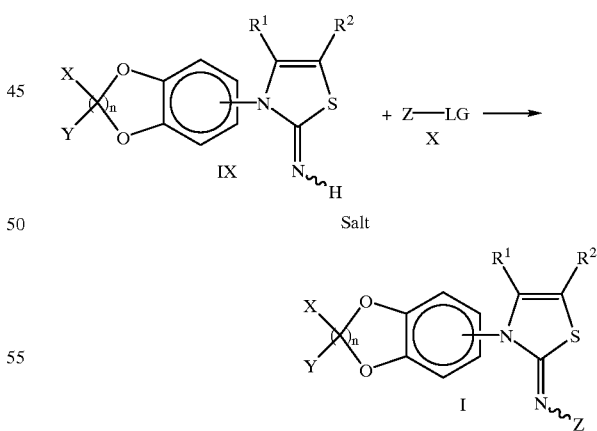

LG (leaving group) is a nucleophilically replaceable leaving group, such as halogen, mesylate, tosylate or acetate.

N-substituted thiazolimine derivatives of the general formula I are generally obtained by reacting thiazolimine derivatives of the general formula IX with from one to ten equivalents of an organic base in an inert solvent, such as methylene chloride, chloroform, tetrahydrofuran, dimethylformamide, toluene, diethyl ether, ethyl acetate, methanol or ethanol, and subsequent reaction with from one to ten equivalents of the radical Z carrying a leaving group (LG). Suitable leaving groups are in particular halogen atoms, ester groups and OH groups. In the last case, it is possible to add dehydrating agents such as dicyclohexylcarbodiimide and related substances to the reaction. During the reaction, the temperature is in a range of from −15° C. to +100° C. Work-up is generally carried out by pouring the reaction mixture into water and subsequently extracting the product of value with an organic solvent such as methylene chloride or ethyl acetate.

The purification of the product of value can be carried out by chromatography, distillation or crystallization.

Alkylcarbonyl: straight-chain or branched alkyl groups having 1 to 10 carbon atoms and attached to the skeleton via a carbonyl group (—CO—);

Haloalkyl: straight-chain or branched alkyl groups having 1 to 4 carbon atoms, the hydrogen atoms in these groups being partly or wholly replaced by halogen atoms as mentioned above, eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Summarized reaction scheme

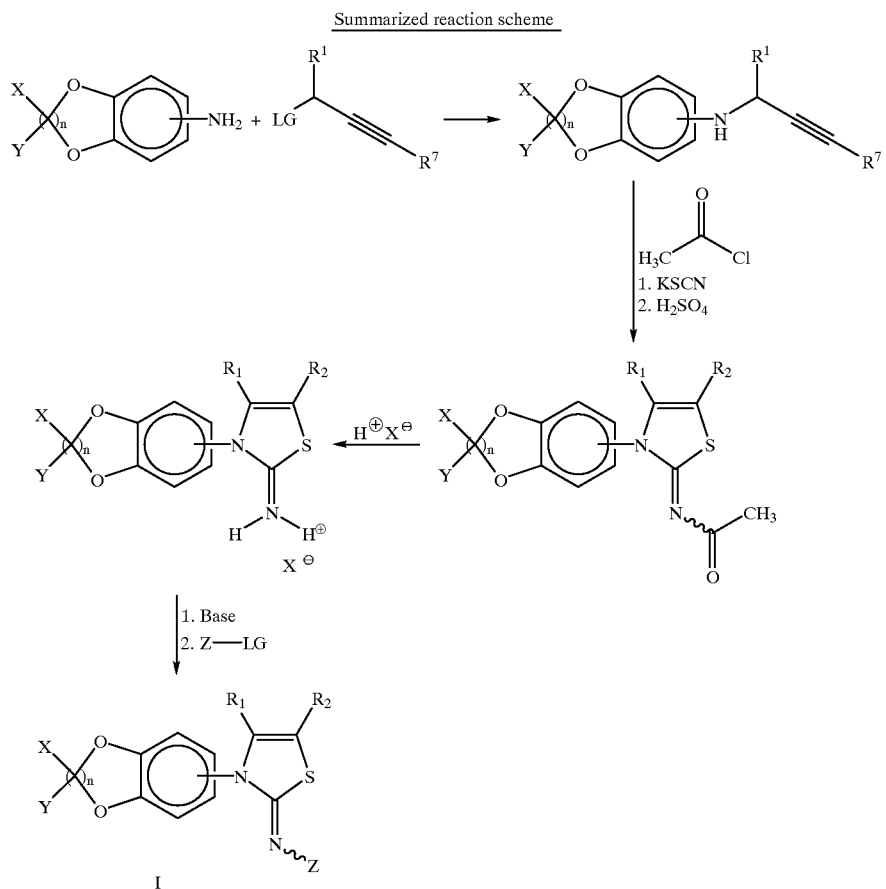

In the definition of the compounds I given at the outset, collective terms were used which are generally representative of the following substituents:

Halogen: fluorine, chlorine, bromine and iodine;

Alkyl: straight-chain or branched alkyl groups having 1 to 4, 6, 8 or 10 carbon atoms, eg. $C_1$–$C_6$-alkyl such as methyl, ethyl, propyl, 1-methylethyl, butyl, 1-methyl-propyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Alkoxy: straight-chain or branched alkyl groups having 1 to 4, 6 or 8 carbon atoms as mentioned above and attached to the skeleton via an oxygen atom (—O—), eg. $C_1$–$C_6$-alkoxy such as methyloxy, ethyloxy, propyloxy, 1-methylethyloxy, butyloxy, 1-methylpropyloxy, 2-methylpropyloxy, 1,1-dimethylethyloxy, pentyloxy, 1-methylbutyloxy, 2-methylbutyloxy, 3-methylbutyloxy, 2,2-dimethylpropyloxy, 1-ethylpropyloxy, hexyloxy, 1,1-dimethylpropyloxy, 1,2-dimethylpropyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy and 1-ethyl-2-methylpropyloxy;

Haloalkoxy: straight-chain or branched alkyl groups having 1 to 4 carbon atoms, the hydrogen atoms in these groups being partly or wholly replaced by halogen atoms as mentioned above, these groups being attached to the skeleton via an oxygen atom;

Alkylthio; straight-chain or branched alkyl groups having 1 to 4, 6 or 8 carbon atoms as mentioned above and attached to the skeleton via a sulfur atom (—S—), eg. $C_1$–$C_6$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

Cycloalkyl: monocyclic alkyl groups having 3 to 7 carbon ring members, eg. cyclopropyl, cyclobutyl, cyclopentyl, cyclohexyl, cycloheptyl;

Cycloalkenyl: as for cycloalkyl, but having at least one double bond;

Alkenyl: straight-chain or branched alkenyl groups having 2 to 6, 8 or 10 carbon atoms and a double bond in any desired position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkenylcarbonyl: straight-chain or branched alkenyl groups having 2 to 10 carbon atoms and a double bond in any desired position and attached to the skeleton via a carbonyl group (—CO—);

Alkynyl: straight-chain or branched alkynyl groups having 2 to 8 or 10 carbon atoms and a triple bond in any desired position, eg. $C_2$–$C_6$-alkynyl such as ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

Alkynylcarbonyl: straight-chain or branched alkynyl groups having 3 to 10 carbon atoms and a triple bond in any desired position and attached to the skeleton via a carbonyl group (—CO—);

Aryl: aromatic mono- or polycyclic hydrocarbon radicals, eg. phenyl, naphthyl and phenanthrenyl;

Hetaryl: aromatic mono- or polycyclic radicals which in addition to carbon ring members may additionally contain one to four nitrogen atoms or one to three nitrogen atoms and one oxygen or one sulfur atom or one oxygen or one sulfur atom, eg. 5-membered hetaryl, containing one to three nitrogen atoms:

5-membered ring hetaryl groups which in addition to carbon atoms may contain one to three nitrogen atoms as ring members, eg. 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered hetaryl, containing one to four nitrogen atoms or one to three nitrogen atoms and one sulfur or oxygen atom or one oxygen or one sulfur atom: 5-membered ring hetaryl groups which in addition to carbon atoms may contain one to four nitrogen atoms or one to three nitrogen atoms and one sulfur or oxygen atom or one oxygen or sulfur atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

benzo-fused 5-membered hetaryl, containing one to three nitrogen atoms or one nitrogen atom and/or one oxygen or sulfur atom: 5-membered ring hetaryl groups which in addition to carbon atoms may contain one to four nitrogen atoms or one to three nitrogen atoms and one sulfur or oxygen atom or one oxygen or one sulfur atom as ring members, and in which two adjacent carbon ring members or one nitrogen and one adjacent carbon ring member may be bridged by a buta-1,3-diene-1,4-diyl group;

5-membered hetaryl attached via nitrogen, containing one to four nitrogen atoms, or benzo-fused 5-membered hetaryl attached via nitrogen, containing one to three nitrogen atoms: 5-membered ring hetaryl groups which in addition to carbon atoms may contain one to four nitrogen atoms or one to three nitrogen atoms as ring members, and in which two adjacent carbon ring members or one nitrogen and one adjacent carbon ring member may be bridged by a buta-1,3-diene-1,4-diyl group, these rings being attached to the skeleton via one of the nitrogen ring members;

6-membered hetaryl, containing one to three or one to four nitrogen atoms: 6-membered ring hetaryl groups which in addition to carbon atoms may contain one to three or one to four nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 6-membered hetaryl, containing one to four nitrogen atoms: 6-membered ring hetaryl groups where two adjacent carbon ring members may be bridged by a buta-1,3-diene-1,4-diyl group, eg. quinoline, isoquinoline, quinazoline, and quinoxaline.

With respect to their biological activity, preference is given to compounds of the formula I where X and Y independently of one another are each hydrogen, halogen or $C_1$–$C_4$-alkyl.

Particular preference is given to compounds of the formula I where X and Y independently of one another are each hydrogen or halogen.

very particular preference is given to compounds of the formula I where X and Y are each fluorine.

Likewise, preference is given to compounds of the formula I where

Z is hydrogen; $C_1$–$C_8$-alkyl, $C_2$–$C_8$-alkenyl, $C_2$–$C_8$-alkynyl, $C_1$–$C_8$-alkoxy or $C_1$–$C_8$-alkylthio, it being possible for these groups to be substituted by one to five halogen atoms or $C_1$–$C_4$-alkoxy; or one of the following groups:

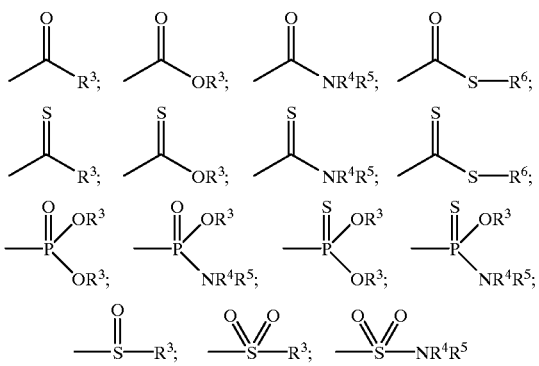

Particular preference is given to compounds of the formula I where

Z is one of the following groups:

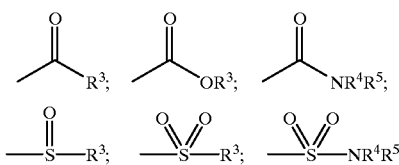

Likewise, preference is given to compounds of the formula I where $R^1$ and $R^2$ are each hydrogen, halogen; or $C_1$–$C_4$-alkyl, $C_2$–$C_4$-alkenyl, $C_2$–$C_4$-alkynyl, it being possible for these groups to be substituted by one to five halogen atoms.

Particular preference is given to compounds of the formula I where $R^1$ is hydrogen, halogen or $C_1$–$C_4$-alkyl, and $R^2$ is hydrogen, halogen; or $C_1$–$C_4$-alkyl which may be substituted by one to five halogen atoms.

Very particular preference is given to compounds of the formula I where $R^1$ is hydrogen and $R^2$ is methyl or ethyl.

Likewise, preference is given to compounds of the formula I where $R^3$ is $C_1$–$C_8$-alkyl, $C_2$–$C_8$-alkenyl, $C_2$–$C_8$-alkynyl, $C_2$–$C_8$-alkylcarbonyl, it being possible for these groups to be substituted by one to eight halogens or by $C_1$–$C_4$-alkoxy; $C_3$–$C_7$-cycloalkyl which may be substituted by one to eight halogen atoms, $C_1$–$C_4$-alkoxy, $C_1$–$C_4$-alkyl or $C_1$–$C_4$-haloalkyl; aryl which may be substituted by $C_1$–$C_4$-alkyl, $C_1$–$C_4$-haloalkyl, $C_1$–$C_4$-alkoxy, $C_1$–$C_4$-haloalkoxy, halogen.

Particular preference is given to compounds of the formula I where $R^3$ is $C_1$–$C_8$-alkyl, $C_2$–$C_8$-alkenyl, $C_2$–$C_8$-alkynyl, $C_2$–$C_8$-alkylcarbonyl, it being possible for these groups to be substituted by one to eight halogens;

or $C_3$–$C_7$-cycloalkyl which may be substituted by one to eight halogen atoms, $C_1$–$C_4$-alkyl or $C_1$–$C_4$-haloalkyl.

Likewise, preference is given to compounds of the formula I where $R^4$ and $R^5$ are each hydrogen; $C_1$–$C_6$-alkyl, $C_2$–$C_6$-alkenyl, $C_2$–$C_6$-alkynyl, it being possible for these groups to be substituted by one to four halogens or by $C_1$–$C_4$-alkoxy; aryl which may be substituted by $C_1$–$C_4$-alkyl, $C_1$–$C_4$-alkoxy, $C_1$–$C_4$-haloalkyl, $C_1$–$C_4$-haloalkoxy or halogen, or $R^4$ and $R^5$ together form a 3- to 7-membered heterocycle which may carry a further heteroatom from the group consisting of N, O and S, may contain a double bond and may be substituted by one to four $C_1$–$C_4$-alkyl, $C_1$–$C_4$-haloalkyl, $C_1$–$C_4$-alkoxy, $C_1$–$C_4$-haloalkoxy, halogen, nitro or cyano groups.

Particular preference is given to compounds of the formula I where $R^4$ and $R^5$ are each hydrogen or $C_1$–$C_6$-alkyl which may be substituted by one to four halogens, or $R^4$ and $R^5$ together form a 3- to 7-membered heterocycle which may carry a further hetero atom from the group consisting of N, O and S, may contain a double bond and may be substituted by $C_1$–$C_4$-alkyl.

Likewise, preference is given to compounds of the formula I where $R^6$ is hydrogen; $C_1$–$C_6$-alkyl, $C_2$–$C_6$-alkenyl, it being possible for these groups to be substituted by one to four halogens or by alkoxy; $C_3$–$C_7$-cycloalkyl which may be substituted by one to four halogens or $C_1$–$C_4$-alkyl, $C_1$–$C_4$-haloalkyl, $C_1$–$C_4$-alkoxy, haloalkoxy; aryl, hetaryl, it being possible for these groups to be substituted by $C_1$–$C_4$-alkyl, $C_1$–$C_4$-haloalkyl, $C_1$–$C_4$-alkoxy, $C_1$–$C_4$-haloalkoxy, halogen, nitro or cyano.

Likewise, preference is given to compounds of the formula I where n is 1.

Furthermore, preference is given to compounds of the formula I where n is 2.

Likewise, preference is given to compounds of the formula I where m is 0.

Furthermore, preference is given to compounds of the formula I where m is 1.

In addition, preference is given to compounds of the formula I where m is 2.

Preference is also given to compounds of the formula I where the thiazolimine substituent is attached to the benzene ring ortho to one of the oxygen atoms of the heterocycle.

Likewise, preference is given to compounds of the formula I where the thiazolimine substituent is attached to the benzene ring meta to one and para to the other oxygen atom of the heterocycle.

Likewise, preference is given to compounds of the formula I where:

X and Y independently of one another are each hydrogen, halogen or $C_1$–$C_4$-alkyl;

Z is hydrogen; $C_1$–$C_8$-alkyl, $C_2$–$C_8$-alkenyl, $C_2$–$C_8$-alkynyl, $C_1$–$C_8$-alkoxy, $C_1$–$C_8$-alkylthio, it being possible for these groups to be substituted by one to five halogens or $C_1$–$C_4$-alkoxy, or is one of the following groups:

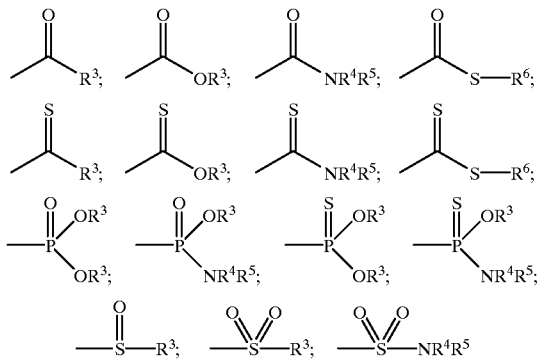

$R^1$ and $R^2$ are each hydrogen, halogen; or $C_1$–$C_4$-alkyl, $C_2$–$C_4$-alkenyl, $C_2$–$C_4$-alkynyl, it being possible for these groups to be substituted by one to five halogen atoms;

$R^3$ is $C_1$–$C_8$-alkyl, $C_2$–$C_o$-alkenyl, $C_2$–$C_8$-alkynyl, $C_2$–$C_8$-alkylcarbonyl, it being possible for these groups to be substituted by one to eight halogens or by $C_1$–$C_4$-alkoxy; $C_3$–$C_7$-cycloalkyl which may be substituted by one to eight halogen atoms, $C_1$–$C_4$-alkoxy, $C_1$–$C_4$-alkyl or $C_1$–$C_4$-haloalkyl; aryl which may be substituted by $C_1$–$C_4$-alkyl, $C_1$–$C_4$-haloalkyl, $C_1$–$C_4$-alkoxy, $C_1$–$C_4$-haloalkoxy or halogen;

$R^4$ and $R^5$ are each hydrogen; $C_1$–$C_6$-alkyl, $C_2$–$C_6$-alkenyl, $C_2$–$C_6$-alkynyl, it being possible for these groups to be substituted by one to four halogen or by $C_1$–$C_4$-alkoxy; aryl which may be substituted by $C_1$–$C_4$-alkyl, $C_1$$C_4$-alkoxy, $C_1$–$C_4$-haloalkyl, $C_1$–$C_4$-haloalkoxy or halogen;

$R^4$ and $R^5$ together form a 3- to 7-membered heterocycle which may carry a further heteroatom from the group consisting of N, O and S, may contain a double bond and may be substituted by $C_1$–$C_4$-alkyl, $C_1$–$C_4$-haloalkyl, $C_1$–$C_4$-alkoxy, $C_1$–$C_4$-haloalkoxy, halogen, nitro or cyano groups;

$R^6$ is hydrogen; $C_1$–$C_6$-alkyl or $C_2$–$C_6$-alkenyl, it being possible for these groups to be substituted by one to four halogens or by alkoxy; $C_3$–$C_7$-cycloalkyl which may be substituted by one to four halogen atoms, $C_1$–$C_4$-alkyl, $C_1$–$C_4$-haloalkyl, $C_1$–$C_4$-alkoxy or haloalkoxy; aryl or hetaryl, it being possible for these groups to be substituted by $C_1$–$C_4$-alkyl, $C_1$–$C_4$-haloalkyl, $C_1$–$C_4$-alkoxy, $C_1$–$C_4$-haloalkoxy, halogen, nitro or cyano;

n is 1 or 2;

m is 0, 1 or 2.

Particular preference is given to compounds of the formula I where:

X and Y independently of one another are each hydrogen or halogen;

Z is one of the groups below:

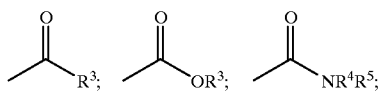

-continued

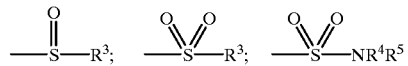

$R^1$ is hydrogen, halogen or $C_1$–$C_4$-alkyl;

$R^2$ is hydrogen, halogen; or $C_1$–$C_4$-alkyl which may be substituted by one to five halogen atoms;

$R^3$ is $C_1$–$C_8$-alkyl, $C_2$–$C_8$-alkenyl, $C_2$–$C_8$-alkynyl or $C_2$–$C_8$-alkylcarbonyl, it being possible for these groups to be substituted by one to eight halogens; $C_3$–$C_7$-cycloalkyl which may be substituted by one to eight halogen atoms, $C_1$–$C_4$-alkyl or $C_1$–$C_4$-haloalkyl;

$R^4$ and $R^5$ are each hydrogen; $C_1$–$C_6$-alkyl which may be substituted by one to four halogen atoms or $R^4$ and $R^5$ together form a 3- to 7-membered heterocycle which may carry a further hetero atom from the group consisting of N, O and S, may contain a double bond and may be substituted by $C_1$–$C_4$-alkyl;

n is 1 or 2;

m is 0.

Very particular preference is given to compounds of formula I where:

X and Y are each fluorine;

Z is one of the groups below:

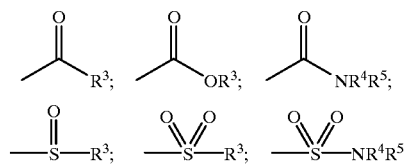

$R^1$ is hydrogen;

$R^2$ is methyl or ethyl;

$R^3$ is $C_1$–$C_8$-alkyl, $C_2$–$C_8$-alkenyl, $C_2$–$C_8$-alkynyl, $C_2$–$C_8$-alkylcarbonyl, it being possible for these groups to be substituted by one to eight halogens;

$C_3C_7$-cycloalkyl which may be substituted by one to eight halogen atoms, $C_1$–$C_4$-alkyl or $C_1$–$C_4$-haloalkyl;

$R^4$ and $R^5$ are each hydrogen; $C_1$–$C_6$-alkyl which may be substituted by one to four halogen atoms or $R^4$ and $R^5$ together form a 3- to 7-membered heterocycle which may carry a further heteroatom from the group consisting of N, O and S, may contain a double bond and may be substituted by $C_1$–$C_4$-alkyl;

n is 1 or 2;

m is 0

Preference is also given to compounds of the formula I where the substituents are selected from a combination of the preferred substituents recited above.

With respect to their use, particular preference is given to the compounds I of the formulae I.1–I.12 listed in the tables below.

Table 1: Compounds 1.1–1.258
Compounds of the general formula I.1,

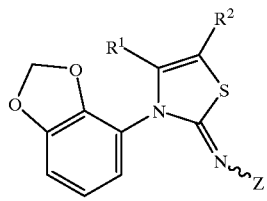

where R¹ is hydrogen, R² is methyl and where for each individual compound the substituent Z corresponds to one row of Table A.

Table 2: Compounds 2.1–2.258
Compounds of the general formula I.2,

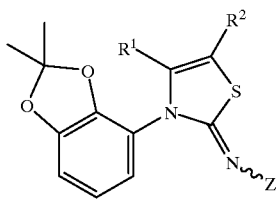

where R¹ is hydrogen, R² is methyl and where for each individual compound the substituent Z corresponds to one row of Table A.

Table 3: Compounds 3.1–3.258
Compounds of the general formula I.3,

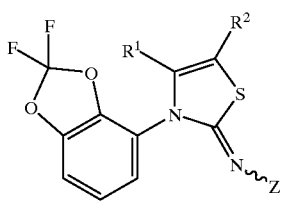

where R¹ is hydrogen, R² is methyl and where for each individual compound the substituent Z corresponds to one row of Table A.

Table 4: Compounds 4.1–4.258
Compounds of the general formula I.3, where R¹ is hydrogen, R² is ethyl and where for each individual compound the substituent Z corresponds to one row of Table A.

Table 5: Compounds 5.1–5.258
Compounds of the general formula I.4,

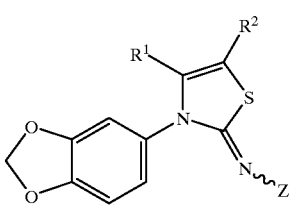

where R¹ is hydrogen, R² is methyl and where for each individual compound the substituent Z corresponds to one row of Table A.

Table 6: Compounds 6.1–6.258
Compounds of the general formula I.5,

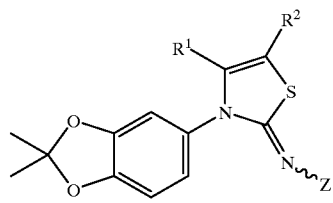

where R¹ is hydrogen, R² is methyl and where for each individual compound the substituent Z corresponds to one row of Table A.

Table 7: Compounds 7.1–7.258
Compounds of the general formula I.6,

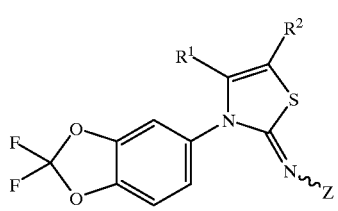

where R¹ is hydrogen, R² is methyl and where for each individual compound the substituent Z corresponds to one row of Table A.

Table 8: Compounds 8.1–8.258
Compounds of the general formula I.6, where R¹ is hydrogen, R² is ethyl and where for each individual compound the substituent Z corresponds to one row of Table A.

Table 9: Compounds 9.1–9.258
Compounds of the general formula I.7,

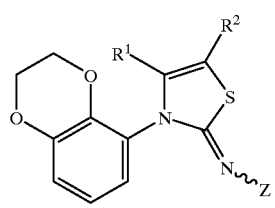

where R¹ is hydrogen, R² is methyl and where for each individual compound the substituent Z corresponds to one row of Table A.

Table 10: Compounds 10.1–10.258
Compounds of the general formula I.8,

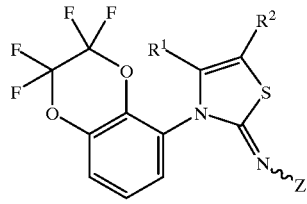

where R¹ is hydrogen, R² is methyl and where for each individual compound the substituent z corresponds to one row of Table A.

Table 11: Compounds 11.1–11.258
Compounds of the general formula I.9,

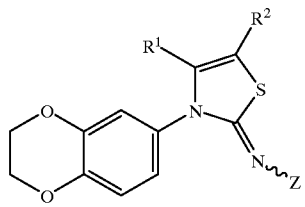

I.9 where $R^1$ is hydrogen, $R^2$ is methyl and where for each individual compound the substituent Z corresponds to one row of Table A.

Table 12: Compounds 12.1–12.258
Compounds of the general formula I.10,

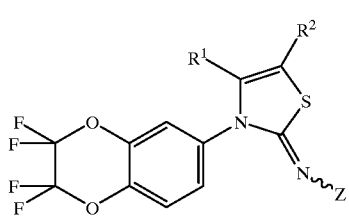

I.10 where $R^1$ is hydrogen, $R^2$ is methyl and where for each individual compound the substituent z corresponds to one row of Table A.

Table 13: Compounds 13.01–13.258
Compounds of the general formula I.3, where $R^1$ is hydrogen, $R^2$ is vinyl and where for each individual compound the substituent Z corresponds to one row of Table A.

Table 14: Compounds 14.1–14.258
Compounds of the general formula I.6, where $R^1$ is hydrogen, $R^2$ is vinyl and where for each individual compound the substituent Z corresponds to one row of Table A.

Table 15: Compounds 15.1–15.258
Compounds of the general formula I.8, where $R^1$ is hydrogen, $R^2$ is vinyl and where for each individual compound the substituent Z corresponds to one row of Table A.

Table 16: Compounds 16.1–16.258
Compounds of the general formula I.10, where $R^1$ is hydrogen, $R^2$ is vinyl and where for each individual compound the substituent Z corresponds to one row of Table A.

TABLE A

| No. | Z |
|---|---|
| 1. | H |
| 2. | Me |
| 3. | Et |
| 4. | n-Prop |
| 5. | i-Prop |
| 6. | n-Bu |
| 7. | s-Bu |
| 8. | i-Bu |
| 9. | t-Bu |
| 10. | —CH=CH$_2$ |
| 11. | —CH$_2$—CH=CH—CH$_3$ (allyl-type, trans) |
| 12. | —CH$_2$—C(CH$_3$)=CH$_2$ with CH$_3$ |
| 13. | —CH$_2$F |
| 14. | —CF$_3$ |
| 15. | —C$_2$F$_5$ |
| 16. | —CH$_2$Cl |
| 17. | —CCl$_3$ |
| 18. | —C$_6$H$_4$-F (para) |
| 19. | —C$_6$H$_5$ |
| 20. | —C$_6$H$_4$-CF$_3$ (meta) |
| 21. | —cyclohexyl |
| 22. | —CH$_2$CH$_2$CH$_2$OMe |
| 23. | —CH$_2$CH$_2$CF$_3$ |
| 24. | —CH(CF$_3$)$_2$ |
| 25. | —C(=O)H |
| 26. | —C(=O)CH$_3$ |
| 27. | —C(=O)Et |
| 28. | —C(=O)n-Prop |

TABLE A-continued
| No. | Z |
|---|---|
| 29. | 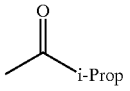 i-Prop |
| 30. | 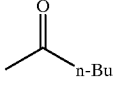 n-Bu |
| 31. | 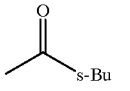 s-Bu |
| 32. | 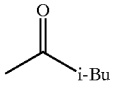 i-Bu |
| 33. | 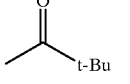 t-Bu |
| 34. | 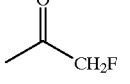 CH$_2$F |
| 35. | 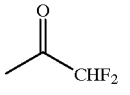 CHF$_2$ |
| 36. | 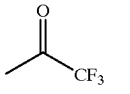 CF$_3$ |
| 37. | 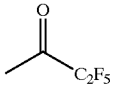 C$_2$F$_5$ |
| 38. | 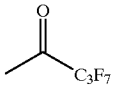 C$_3$F$_7$ |
| 39. | 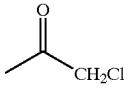 CH$_2$Cl |
| 40. | 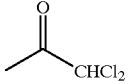 CHCl$_2$ |
| 41. | 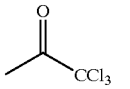 CCl$_3$ |
| 42. | 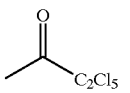 C$_2$Cl$_5$ |
| 43. | 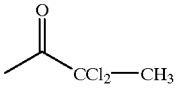 CCl$_2$—CH$_3$ |
| 44. | 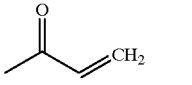 CH$_2$ |
| 45. | 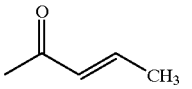 CH$_3$ |
| 46. | 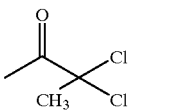 CH$_3$, Cl, Cl |
| 47. |  Cl |
| 48. |  Ph |
| 49. | 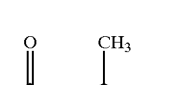 CH$_3$ |
| 50. |  CH$_3$ |
| 51. | 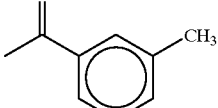 CH$_3$ |
| 52. |  CH$_3$, CH$_3$ |
| 53. |  CH$_3$, CH$_3$ |

TABLE A-continued
| No. | Z |
|---|---|
| 54. | 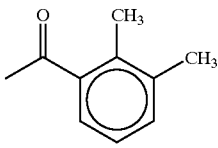 |
| 55. | 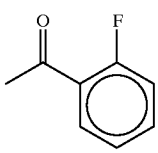 |
| 56. | 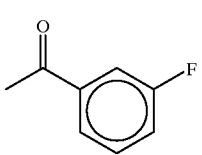 |
| 57. | 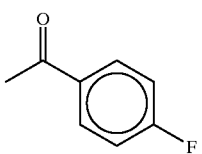 |
| 58. | 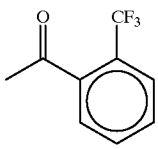 |
| 59. | 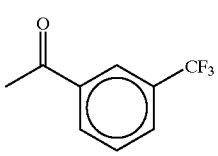 |
| 60. | 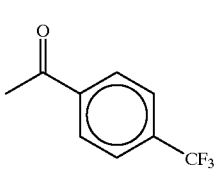 |
| 61. | 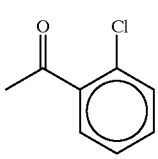 |
| 62. | 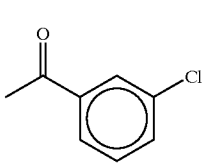 |
TABLE A-continued
| No. | Z |
|---|---|
| 63. | 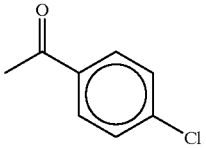 |
| 64. | 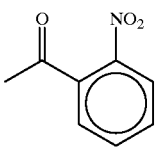 |
| 65. | 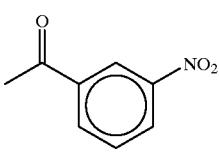 |
| 66. | 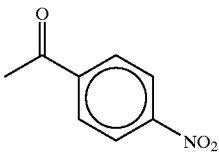 |
| 67. | 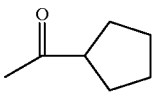 |
| 68. | 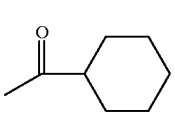 |
| 69. | 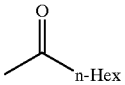 |
| 70. | 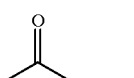 |
| 71. | 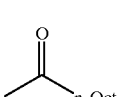 |
| 72. | 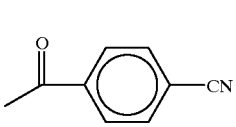 |
| 73. | 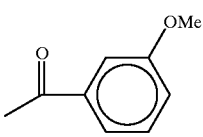 |

TABLE A-continued

| No. | Z |
|---|---|
| 74. | −C(=O)−O−Me |
| 75. | −C(=O)−O−Et |
| 76. | −C(=O)−O−n-Prop |
| 77. | −C(=O)−O−i-Prop |
| 78. | −C(=O)−O−n-Bu |
| 79. | −C(=O)−O−s-Bu |
| 80. | −C(=O)−O−i-Bu |
| 81. | −C(=O)−O−t-Bu |
| 82. | −C(=O)−O−n-Pent |
| 83. | −C(=O)−O−n-Hex |
| 84. | −C(=O)−O−n-Hept |
| 85. | −C(=O)−O−n-Oct |
| 86. | −C(=O)−O−cyclopentyl |
| 87. | −C(=O)−O−cyclohexyl |
| 88. | −C(=O)−O−CH=CH$_2$ |
| 89. | −C(=O)−O−CH=CH−CH$_3$ |
| 90. | −C(=O)−O−C(CH$_3$)=CH$_2$ |
| 91. | −C(=O)−O−CH$_2$−CH=CH$_2$ |
| 92. | −C(=O)−O−CH$_2$−CH=CH−CH$_3$ |
| 93. | −C(=O)−O−CH$_2$−CH=C(CH$_3$)$_2$ |
| 94. | −C(=O)−O−cyclohex-3-enyl |
| 95. | −C(=O)−O−CH$_2$−CH$_2$−F |
| 96. | −C(=O)−O−CH$_2$−CHF$_2$ |
| 97. | −C(=O)−O−CH$_2$−CF$_3$ |

TABLE A-continued
| No. | Z |
|---|---|
| 98. | 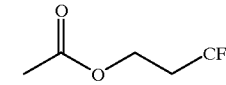 |
| 99. | 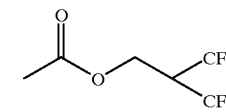 |
| 100. | 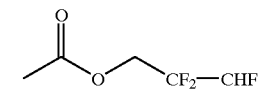 |
| 101. | 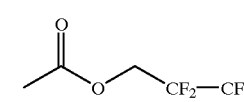 |
| 102. | 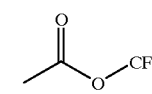 |
| 103. | 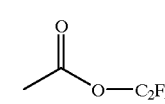 |
| 104. | 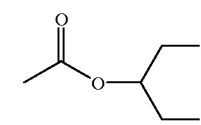 |
| 105. | 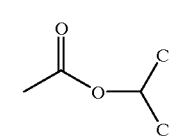 |
| 106. | 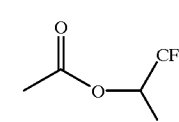 |
| 107. | 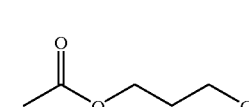 |
| 108. | 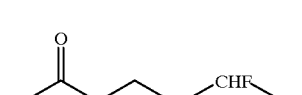 |
| 109. | 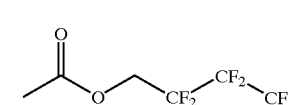 |
| 110. | 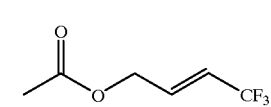 |
TABLE A-continued
| No. | Z |
|---|---|
| 111. | 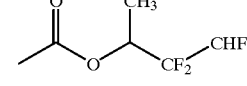 |
| 112. | 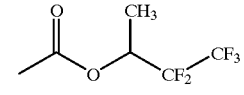 |
| 113. | 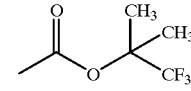 |
| 114. | 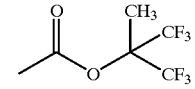 |
| 115. | 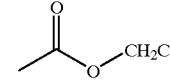 |
| 116. | 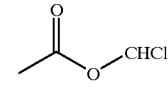 |
| 117. | 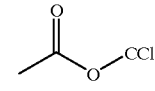 |
| 118. | 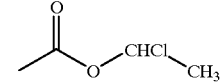 |
| 119. | 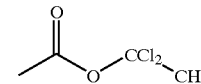 |
| 120. | 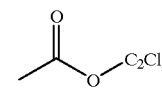 |
| 121. | 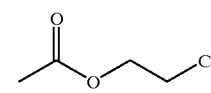 |
| 122. | 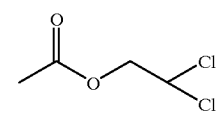 |
| 123. |  |

TABLE A-continued

| No. | Z |
|---|---|
| 124. | acetate of 3-chloropropyl |
| 125. | acetate of 1-chloropropan-2-yl |
| 126. | acetate of 2-methyl-1,1,1-trichloropropan-2-yl |
| 127. | acetate of 2,2,2-trichloroethyl |
| 128. | acetate of 1,1,1,2,2,2-hexachloroethyl substituted |
| 129. | acetate of 1,1-dichloropropan-2-yl |
| 130. | acetate of 2,2,3,3,3-pentachloropropyl |
| 131. | acetate of 2,2-dichlorocyclopropyl |
| 132. | acetate of 2-bromoethyl |
| 133. | acetate of 2,2-dibromoethyl |
| 134. | acetate of tribromomethyl |
| 135. | acetate of 3-bromopropyl |
| 136. | phenyl acetate |
| 137. | 2-methylphenyl acetate |
| 138. | 3-methylphenyl acetate |
| 139. | 4-methylphenyl acetate |
| 140. | 2,4-dimethylphenyl acetate |
| 141. | 3,5-dimethylphenyl acetate |
| 142. | 2-fluorophenyl acetate |
| 143. | 3-fluorophenyl acetate |
| 144. | 4-fluorophenyl acetate |
| 145. | 2-chlorophenyl acetate |
| 146. | 3-chlorophenyl acetate |

TABLE A-continued

| No. | Z |
|---|---|
| 147. | acetate of 4-chlorophenol |
| 148. | acetate of 2-bromophenol |
| 149. | acetate of 3-bromophenol |
| 150. | acetate of 4-bromophenol |
| 151. | acetate of 2-nitrophenol |
| 152. | acetate of 3-nitrophenol |
| 153. | acetate of 4-nitrophenol |
| 154. | benzyl acetate |
| 155. | 1-naphthyl acetate |
| 156. | 2-methoxyethyl acetate |
| 157. | 2-ethoxyethyl acetate |
| 158. | 3-methoxypropyl acetate |
| 159. | acetic trifluoroacetic anhydride |
| 160. | acetic anhydride |
| 161. | acetic propionic anhydride |
| 162. | acetic pentafluoropropionic anhydride |
| 163. | acetic butyric anhydride |
| 164. | acetamide ($NH_2$) |
| 165. | N-methylacetamide (NHMe) |
| 166. | N,N-dimethylacetamide ($NHMe_2$) |
| 167. | N,N-diethylacetamide ($NEt_2$) |
| 168. | N,N-di-n-propylacetamide ($N(n\text{-}Prop)_2$) |
| 169. | N,N-diphenylacetamide ($N(Ph)_2$) |
| 170. | N-methyl-N-phenylacetamide |
| 171. | N,N-diisopropylacetamide ($N(i\text{-}Prop)_2$) |

TABLE A-continued
| No. | Z |
|---|---|
| 172. | 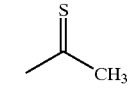 |
| 173. | 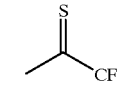 |
| 174. | 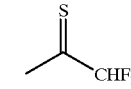 |
| 175. | 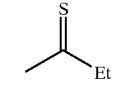 |
| 176. | 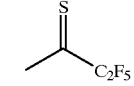 |
| 177. | 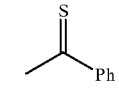 |
| 178. | |
| 179. | |
| 180. | |
| 181. | |
| 182. | |
| 183. | |
| 184. | ![](CH$_3$, C=S) |
| 185. | ![](CF$_3$, C=S) |
| 186. | ![](CHF$_2$, C=S) |
| 187. | ![](Et, C=S) |
| 188. | ![](C$_2$F$_5$, C=S) |
| 189. | ![](Ph, C=S) |
| 190. | ![](O—Ph, C=S) |
| 191. | 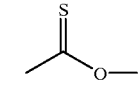 |
| 192. | 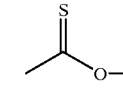 |
| 193. | ![](O—CH$_3$, C=S) |
| 194. | ![](O—CF$_3$, C=S) |
| 195. | ![](O—C$_2$F$_5$, C=S) |
| 196. | ![](O—CH$_2$—CF$_3$, C=S) |

TABLE A-continued
| No. | Z |
|---|---|
| 197. | 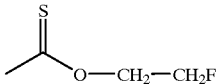 |
| 198. | 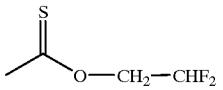 |
| 199. | 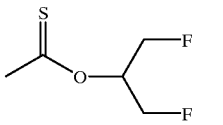 |
| 200. | 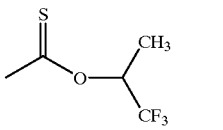 |
| 201. | 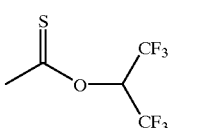 |
| 202. | 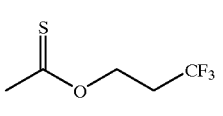 |
| 203. | 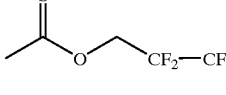 |
| 204. | 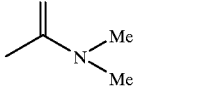 |
| 205. | 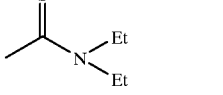 |
| 206. | 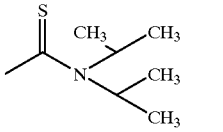 |
| 207. | 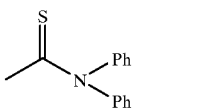 |
| 208. | 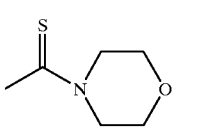 |
| 209. | 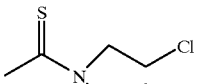 |
| 210. |  |
| 211. |  |
| 212. |  |
| 213. | 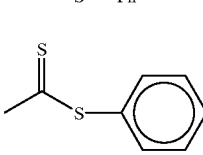 |
| 214. | 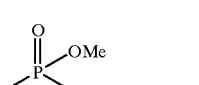 |
| 215. | 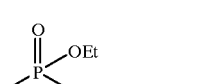 |
| 216. | 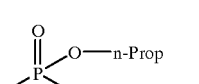 |
| 217. | 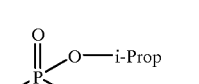 |
| 218. | 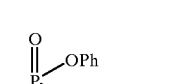 |
| 219. | 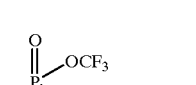 |
| 220. | 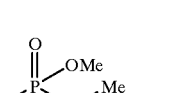 |
| 221. | 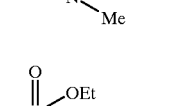 |

6,165,943
TABLE A-continued
| No. | Z |
|-----|---|
| 222. | 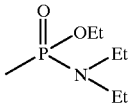 |
| 223. | 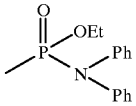 |
| 224. | 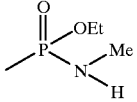 |
| 225. | 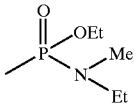 |
| 226. | 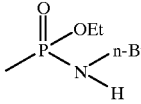 |
| 227. | 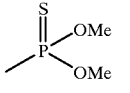 |
| 228. | 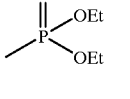 |
| 229. | 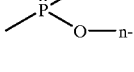 |
| 230. | 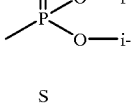 |
| 231. | 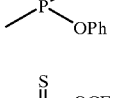 |
| 232. | 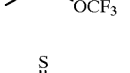 |
| 233. | 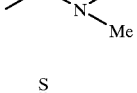 |
| 234. | 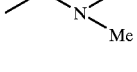 |
TABLE A-continued
| No. | Z |
|-----|---|
| 235. | 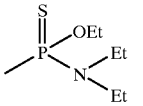 |
| 236. | 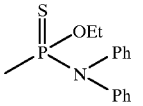 |
| 237. | 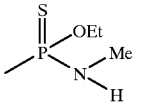 |
| 238. | 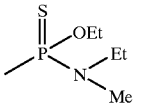 |
| 239. | 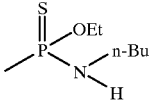 |
| 240. | 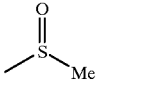 |
| 241. | 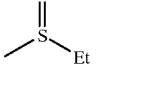 |
| 242. | 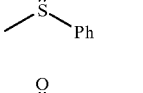 |
| 243. | 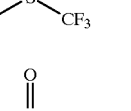 |
| 244. | 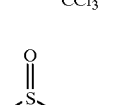 |
| 245. | 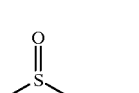 |
| 246. | 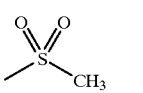 |
| 247. |  |

TABLE A-continued

| No. | Z |
|---|---|
| 248. |  —S(O)(O)—Et |
| 249. | —S(O)(O)—Ph |
| 250. | —S(O)(O)—CF₃ |
| 251. | —S(O)(O)—CCl₃ |
| 252. | —S(O)(O)—C₂F₅ |
| 253. | —S(O)(O)—C₂Cl₅ |
| 254. | —S(O)(O)—C₆H₄-F |
| 255. | —S(O)(O)—C₆H₄-CH₃ |
| 256. | —S(O)(O)—NH₂ |
| 257. | —S(O)(O)—N(H)(Me) |
| 258. | —S(O)(O)—N(CH₃)₂ |

PREPARTION EXAMPLES

1. At 20–25° C., 53.3 g of an 80% strength solution of propargyl bromide in toluene (≐0.36 mol of propargyl bromide) are added dropwise to a solution of 120 g (0.67 mol) of 4-amino-2,2-difluorobenzo-1,3-dioxole in 150 ml of toluene. After 2 hours at 80° C., the reaction mixture is cooled to room temperature and the precipitate is filtered off with suction and washed with n-hexane. The filtrate is concentrated under reduced pressure and the residue is purified over silica gel using cyclohexane/ethyl acetate mixtures and then-crystallized from pentane. 33.2 g (44% of theory) of N-propargyl-4-amino-2,2-difluorobenzo-1,3-dioxole of mp.: 66–68° C. are obtained in this manner. NMR: (CDCl₃): 2.25 (t, 1H); 3.9 (2*s, 3H); 6.30 (dd, 1H); 6.50 (d, 1H); 6.85 (d, 1H)

2. 8.75 g of acetyl chloride (0.087 mol) are dissolved in 150 ml of absolute acetonitrile and, at 0° C., mixed with 8.75 g (0.09 mol) of potassium thiocyanate. After 6 hours at 0° C. 18.3 g of N-propargyl-4-amino-2,2-difluorobenzo-1,3-dioxole (0.087 mol) in 20 ml of CH₃CN are added dropwise. After the addition, the mixture is stirred at room temperature for 16 hours. The mixture is subsequently concentrated under reduced pressure and the residue is washed with ethyl acetate. The organic phases are washed with water (3 times) and with saturated NaCl solution (once) and then dried over Na₂SO₄. At 0° C., the residue which is obtained after the evaporation of the solvent is added to 61 ml of conc. sulfuric acid and stirred at 0° C. for 30 min and then at 20° C. for 1 hour. The solution is subsequently poured into ice-water and neutralized at 20–25° C. using 50% strength aqueous sodium hydroxide solution. The aqueous phase is subsequently extracted 3 times with methylene chloride and the combined organic phases are washed with water (twice) and with saturated NaCl solution (once). After drying and evaporation of the solvent, the residue is recrystallized from diethyl ether.

11.4 g of 4-(N'-acetyl-2'-imino-5'-methylthiazol-3-yl)-2,2-difluorobenzo-1,3-dioxole (0.036 mol; 42% of theory] of mp.: =203–205° C. are obtained in this manner.

¹H-NMR: CDCl₃: 2.22 (s, 3H); 2.30 (s, 3H); 6.65 (s, 1H); 7.18 (m, 2H); 7.30 (s, 1H)

3. 21.5 g (0.069 mol) of 4-(N'-acetyl-2'-imino-5'-methylthiazol-3-yl)-2,2-difluorobenzo-1,3-dioxole are dissolved in 111 ml of ethanol and 111 ml of water and treated with 22.1 ml of conc. hydrochloric acid. The reaction mixture is heated under reflux for 3 hours and then evaporated to dryness. The solid is taken up twice in methylene chloride and isolated again.

21.2 g of 4-(2'-imino-5'-methylthiazol-3-yl)-2,2-difluorobenzo-1,3-dioxole hydrochloride (100% of theory) of mp.: >220° C. (decomposition) are obtained in this manner.

¹H (DMSO): 2.25 (s, 3H); 7.25 (s, 1H); 7.50 (d, 1H); 7.72 (d, 1H); 7.90 (s, 1H); 9.70 (s, br. 2H)

4. Active compounds a) 1.2 g of 4-(2'-imino-5'-methylthiazol-3-yl)-2,2-difluorobenzo-1,3-dioxole hydrochloride are dissolved in 40 ml of ethyl acetate and, at 0° C., admixed first with 1.2 g of triethylamine (0.0119 mol) and then with 0.47 g of isopropenyl chloroformate (0.0039 mol). The reaction mixture is stirred at 20–25° C. for 16 hours. A further 150 ml of ethyl acetate are then added, the precipitate is filtered off with suction and the filtrate is washed with water (3 times) and with saturated NaCl solution (once). The organic phase is dried, the solvent is evaporated under reduced pressure and the residue is purified by silica gel column chromatography using cyclohexane/ethyl acetate mixtures as eluent.

0.75 g of 4-(N'-isopropenyloxycarbonyl-2'-imino-5-methylthiazol-3-yl)-2,2-difluorobenzo-1,3-dioxole (54% of theory) of mp.: 82–84° C. is obtained in this manner.

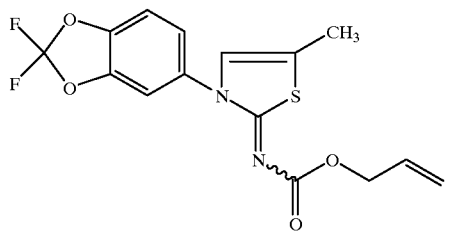

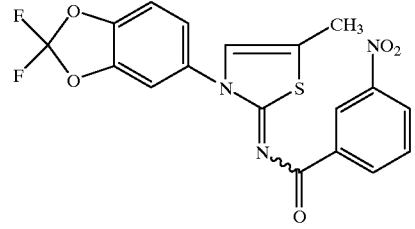

b) 1.2 g of 4-(2'-imino-5'-methylthiazol-3-yl)-2,2-difluorobenzo-1,3-dioxole hydrochloride (0.0039 mol) are dissolved in 40 ml of ethyl acetate and admixed at 0° C. first with 1.2 g of triethylamine (0.0119 mol) and then with 0.85 g of di-tert-butyl dicarbonate (0.0039 mol). The reaction mixture is then stirred at 20–25° C. for 3 hours and then admixed with 150 ml of ethyl acetate. The precipitate is filtered off with suction and the filtrate is washed with water (3 times) and with saturated NaCl solution (once). The organic phase is dried, the solvent is evaporated under reduced pressure and the residue is purified by silica gel column chromatography using cyclohexane/ethyl acetate mixtures.

0.95 g of 4-(N'-tert-butyloxycarbonyl-2'-imino-5'-methylthiazol-3-yl)-2,2-difluorobenzo-1,3-dioxole (66% of theory) is obtained as an oil in this manner.

NMR: CDCl$_3$: 1.50 (s, 9H); 2.25 (s, 3H); 6.65 (s, 1H); 7.12 (m; 2H); 7.32 (s, 1H)

d) 1.0 g of 4-(2'-imino-5'-methylthiazol-3-yl)-2,2-difluorobenzo-1,3-dioxole hydrochloride (0.0033 mol) is dissolved in 40 ml of tetrahydrofuran and mixed with 1.0 g of triethylamine (0.01 mol) and 0.62 g of phenyl chlorodithioformate (0.0033 mol). The reaction mixture is subsequently stirred at 20–25° C. for 16 hours, concentrated using a rotary evaporator, taken up in 100 ml of ethyl acetate and washed with water (3 times) and with saturated NaCl solution (once). The organic phase is dried, the solvent is removed under reduced pressure and the crude product is purified by silica gel column chromatography using cyclohexane/ethyl acetate mixtures.

0.42 g of 4-(N'-phenyldithioformyl-2'-imino-5'-methylthiazol-3-yl)-2,2-difluorobenzo-1,3-dioxole (30% of theory) is obtained as an oil in this manner.

NMR: CDCl$_3$: 2.30 (s, 3H); 6.85 (m, 3H); 7.15 (m, 2H); 7.25 (m, 3H)

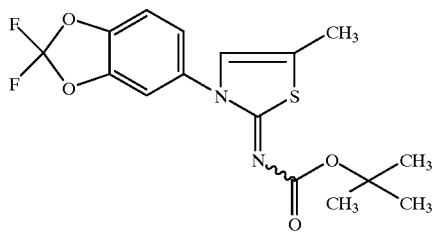

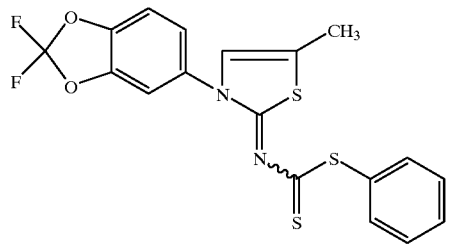

c) 0.8 g of 4-(2'-imino-5'-methylthiazol-3-yl)-2,2-difluorobenzo-1,3-dioxole hydrochloride is dissolved in 30 ml of chloroform and mixed with 4.1 g (0.04 mol) of triethylamine, 1.4 g of N-ethyl-N'-(3-dimethylamino-propyl) carbodiimide hydrochloride (0.0074 mol) and 3.0 g of 3-nitrobenzoic acid. The reaction mixture is subsequently heated under reflux for 5 hours. After cooling, the mixture is washed with dilute hydrochloric acid and dilute potassium carbonate solution and the organic phase is dried. After removal of the solvent under reduced pressure, the crude product is purified by silica gel column chromatography using cyclohexane/ethyl acetate mixtures.

0.7 g of 4-[N'-(3"-nitrobenzoyl)-2'-imino-5'methylthiazol-3-yl]-2,2-difluorobenzo-1,3-dioxole (64% of theory) of mp.: 211–213° C. is obtained in this manner.

e) 1.5 g of 4-(2'-imino-5'-methylthiazol-3-yl)-2,2-difluorobenzo-1,3-dioxole hydrochloride (0.005 mol) are dissolved in 90 ml of methylene chloride and admixed with 0.94 g of diethyl chlorothiophosphate (0.005 mol) and 1.01 g of triethylamine (0.01 mol). The reaction mixture is stirred at 20–25° C. for 3 hours and then extracted with dilute hydrochloric acid. The organic phase is then washed with water (3 times) and with saturated NaCl solution (once). The organic phase is dried over Na$_2$SO$_4$, the solvent is evaporated under reduced pressure and the residue is purified by silica gel column chromatography using cyclohexane/ethyl acetate mixtures.

1.0 g of 4-[(N'-diethoxythiophosphoramido)-2'-imino-5'-methylthiazol-3-yl]-2,2-difluorobenzo-1,3-dioxole (47% of theory) of mp.: 90–92° C. is obtained in this manner.

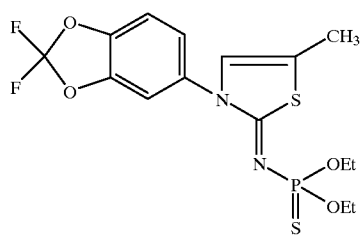

f) 1.0 g of 4-(2'-imino-5'-methylthiazol-3-yl)-2,2-difluorobenzo-1,3-dioxole hydrochloride (0.0033 mol) is dissolved in 40 ml of ethyl acetate and, at 0° C., admixed with 1.0 g of triethylamine (0.01 mol) and 0.95 g of trifluoromethanesulfonic anhydride (0.0033 mol). The mixture is subsequently stirred at 20–25° C. for 3 hours. The reaction mixture is then admixed with 150 ml of ethyl acetate and the precipitate is filtered off with suction. The filtrate is washed with water (3 times) and with saturated NaCl solution (once) and then dried over Na$_2$SO$_4$. The solvent is removed under reduced pressure and the residue is purified by silica gel column chromatography using cyclohexane/ethyl acetate mixtures.

1.1 g of 4-(N'-trifluoromethylsulfonyl-2'-imino-5'-methylthiazol-3-yl)-2,2-difluorobenzo-1,3-dioxole (83% of theory) of mp.: 124–135° C. are obtained.

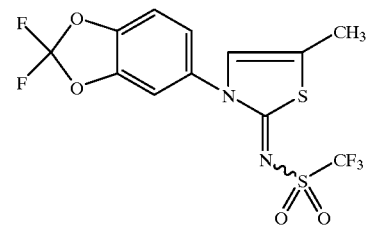

TABLE 17 synthesized compounds

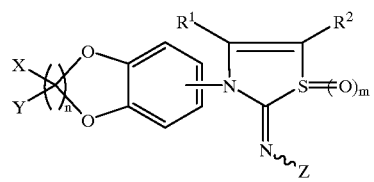

| No. | X | Y | n | m | Ring position | Z | R$^1$ | R$^2$ | R$^3$ |
|---|---|---|---|---|---|---|---|---|---|
| 17.1 | F | F | 1 | 0 | m,p | H | H | Me | — |
| 17.2 | F | F | 1 | 0 | m,p | C(O)R$^3$ | H | Me | CH$_3$ |
| 17.3 | F | F | 1 | 0 | m,p | C(O)R$^3$ | H | Me | CHF$_2$ |
| 17.4 | F | F | 1 | 0 | m,p | C(O)R$^3$ | H | Me | CF$_3$ |
| 17.5 | F | F | 1 | 0 | m,p | C(O)R$^3$ | H | Me | C$_2$F$_5$ |
| 17.6 | F | F | 1 | 0 | m,p | C(O)R$^3$ | H | Me | CH$_2$Cl |
| 17.7 | F | F | 1 | 0 | m,p | C(O)R$^3$ | H | Me | CH=CHCH$_3$ |

TABLE 17-continued
synthesized compounds
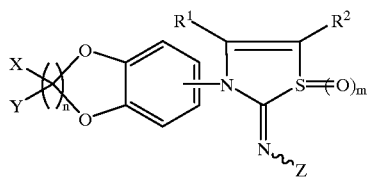
| No. | X | Y | n | m | pos | R³ group | R¹ | R² | Z |
|---|---|---|---|---|---|---|---|---|---|
| 17.8 | F | F | 1 | 0 | m,p |  | H | Me |  |
| 17.9 | F | F | 1 | 0 | m,p |  | H | Me | 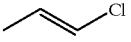 |
| 17.10 | F | F | 1 | 0 | m,p |  | H | Me | 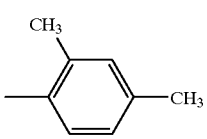 |
| 17.11 | F | F | 1 | 0 | m,p |  | H | Me | 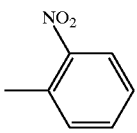 |
| 17.12 | F | F | 1 | 0 | m,p | 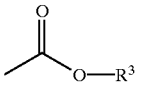 | H | Me | Et |
| 17.13 | F | F | 1 | 0 | m,p | 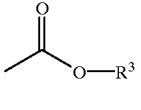 | H | Me | n-Prop |
| 17.14 | F | F | 1 | 0 | m,p | 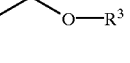 | H | Me | i-Prop |
| 17.15 | F | F | 1 | 0 | m,p | 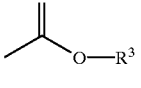 | H | Me | n-Bu |
| 17.16 | F | F | 1 | 0 | m,p | 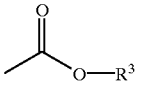 | H | Me | s-Bu |
| 17.17 | F | F | 1 | 0 | m,p | 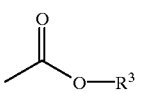 | H | Me | i-Bu |
| 17.18 | F | F | 1 | 0 | m,p | 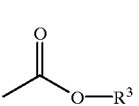 | H | Me | t-Bu |

TABLE 17-continued synthesized compounds

| No. | X | Y | n | m | pos | Z | R1 | R2 | R3 |
|---|---|---|---|---|---|---|---|---|---|
| 17.19 | F | F | 1 | 0 | m,p | -C(=O)-O-R3 | H | Me | n-Hex |
| 17.20 | F | F | 1 | 0 | m,p | -C(=O)-O-R3 | H | Me | n-Hept |
| 17.21 | F | F | 1 | 0 | m,p | -C(=O)-O-R3 | H | Me | n-Oct |
| 17.22 | F | F | 1 | 0 | m,p | -C(=O)-O-R3 | H | Me | cyclopentyl-CH2- |
| 17.23 | F | F | 1 | 0 | m,p | -C(=O)-O-R3 | H | Me | cyclohexyl-CH2- |
| 17.24 | F | F | 1 | 0 | m,p | -C(=O)-O-R3 | H | Me | CH2=C(CH3)-CH2- |
| 17.25 | F | F | 1 | 0 | m,p | -C(=O)-O-R3 | H | Me | CH2=CH-CH2-CH2- |
| 17.26 | F | F | 1 | 0 | m,p | -C(=O)-O-R3 | H | Me | -CH2-CH2-CH2F |
| 17.27 | F | F | 1 | 0 | m,p | -C(=O)-O-R3 | H | Me | -CH2-CH2-CF3 |
| 17.28 | F | F | 1 | 0 | m,p | -C(=O)-O-R3 | H | Me | -CH2-CH(F)-CH2F |
| 17.29 | F | F | 1 | 0 | m,p | -C(=O)-O-R3 | H | Me | -CH(CH3)-CF3 (as -CH2-CH(CH3)-CF3) |
| 17.30 | F | F | 1 | 0 | m,p | -C(=O)-O-R3 | H | Me | -CH(CH3)-CH2Cl |

TABLE 17-continued synthesized compounds

| | | | | | | | R¹ | R² | Z |
|---|---|---|---|---|---|---|---|---|---|
| 17.31 | F | F | 1 | 0 | m,p | —C(O)OR³ | H | Me | —CH₂CH₂Cl |
| 17.32 | F | F | 1 | 0 | m,p | —C(O)OR³ | H | Me | phenyl |
| 17.33 | F | F | 1 | 0 | m,p | —C(O)OR³ | H | Me | 4-methylphenyl |
| 17.34 | F | F | 1 | 0 | m,p | —C(O)OR³ | H | Me | 4-bromophenyl |
| 17.35 | F | F | 1 | 0 | m,p | —C(O)OR³ | H | Me | 2-nitrophenyl |
| 17.36 | F | F | 1 | 0 | m,p | —C(O)OR³ | H | Me | 1-naphthyl |
| 17.37 | F | F | 1 | 0 | m,p | —C(O)OR³ | H | Me | —CH₂CH₂Ph |
| 17.38 | F | F | 1 | 0 | m,p | —C(O)OR³ | H | Me | —CH₂CH₂CH₂OCH₃ |
| 17.39 | F | F | 1 | 0 | m,p | —C(O)S—R6 | H | Me | — |
| 17.40 | F | F | 1 | 0 | m,p | —C(S)OR³ | H | Me | phenyl |
| 17.41 | F | F | 1 | 0 | m,p | —C(S)OR³ | H | Me | 4-methylphenyl |

TABLE 17-continued synthesized compounds

| | | | | | | R¹ group | R² | | Z |
|---|---|---|---|---|---|---|---|---|---|
| 17.42 | F | F | 1 | 0 | m,p | —C(=S)—OR³ | H | Me | 4-F-C₆H₄ |
| 17.43 | F | F | 1 | 0 | m,p | —C(=S)—S—R6 | H | Me | — |
| 17.44 | F | F | 1 | 0 | m,p | —P(=S)(OR³)(OR³) | H | Me | Et |
| 17.45 | F | F | 1 | 0 | m,p | —S(=S)(=O)R³ | H | Me | CF₃ |
| 17.46 | F | F | 1 | 0 | m,p | —C(=O)N(R⁴)(R⁵) | H | Me | — |
| 17.47 | F | F | 1 | 0 | m,p | —C(=O)N(R⁴)(R⁵) | H | Me | — |
| 17.48 | F | F | 1 | 0 | m,p | —C(=O)OR³ | H | Me | CH(CF₃)₂ |
| 17.49 | F | F | 1 | 0 | o | H | H | Me | — |
| 17.50 | F | F | 1 | 0 | o | —C(=O)R³ | H | Me | CH₃ |
| 17.51 | F | F | 1 | 0 | o | —C(=O)R³ | H | Me | CHF₂ |
| 17.52 | F | F | 1 | 0 | o | —C(=O)R³ | H | Me | CF₃ |
| 17.53 | F | F | 1 | 0 | o | —C(=O)R³ | H | Me | C₂F₅ |

TABLE 17-continued synthesized compounds

[Structure: benzodioxole-substituted thiazoline with R¹, R², S(=O)ₘ, N-Z, and X,Y substituents]

| No. | X | Y | n | m | | R¹ | | R² | Z |
|---|---|---|---|---|---|---|---|---|---|
| 17.54 | F | F | 1 | 0 | o | C(=O)R³ | H | Me | 2,4-dimethylphenyl |
| 17.55 | F | F | 1 | 0 | o | C(=O)R³ | H | Me | CH=CH-CH₃ |
| 17.56 | F | F | 1 | 0 | o | C(=O)NR⁴R⁵ | H | Me | — |
| 17.57 | F | F | 1 | 0 | o | C(=O)OR³ | H | Me | Et |
| 17.58 | F | F | 1 | 0 | o | C(=O)OR³ | H | Me | n-Prop |
| 17.59 | F | F | 1 | 0 | o | C(=O)OR³ | H | Me | i-Prop |
| 17.60 | F | F | 1 | 0 | o | C(=O)OR³ | H | Me | n-Bu |
| 17.61 | F | F | 1 | 0 | o | C(=O)OR³ | H | Me | cyclopentyl |
| 17.62 | F | F | 1 | 0 | o | C(=O)OR³ | H | Me | cyclohexyl |
| 17.63 | F | F | 1 | 0 | o | C(=O)OR³ | H | Me | s-Bu |
| 17.64 | F | F | 1 | 0 | o | C(=O)OR³ | H | Me | t-Bu |

TABLE 17-continued synthesized compounds

| No. | X | Y | n | m | pos | R³ group | R¹ | R² | Z |
|---|---|---|---|---|---|---|---|---|---|
| 17.65 | F | F | 1 | 0 | o | CH₃C(O)OR³ | H | Me | CH₂CH₂F |
| 17.66 | F | F | 1 | 0 | o | CH₃C(O)OR³ | H | Me | CH₂CH₂CF₃ |
| 17.67 | F | F | 1 | 0 | o | CH₃C(O)OR³ | H | Me | i-Bu |
| 17.68 | F | F | 1 | 0 | o | CH₃C(O)OR³ | H | Me | CH(CH₂F)₂ |
| 17.69 | F | F | 1 | 0 | m,p | CH₃C(O)R³ | H | Me | CCl₃ |
| 17.70 | F | F | 1 | 0 | m,p | CH₃C(O)R³ | H | Me | CClF₂ |
| 17.71 | F | F | 1 | 0 | m,p | CH₃ | H | Me | — |
| 17.72 | F | F | 1 | 0 | m,p | CH₃C(O)O—R³ | H | Me | CH₂—CF₂—CF₂H |
| 17.73 | F | F | 1 | 0 | m,p | CH₃C(O)NR⁴R⁵ | H | Me | — |
| 17.74 | F | F | 1 | 0 | m,p | CH₃C(O)NR⁴R⁵ | H | Me | — |
| 17.75 | F | F | 1 | 0 | m,p | CH₃C(O)R³ | H | Et | CHF₂ |
| 17.76 | F | F | 1 | 0 | m,p | CH₃C(O)R³ | H | Et | CF₃ |

TABLE 17-continued synthesized compounds

| No. | X | Y | n | m | pos | R¹ | R² | Z |
|---|---|---|---|---|---|---|---|---|
| 17.77 | F | F | 1 | 0 | m,p | ![acetate O-R³] | H | Et | CH₂CH₂F |
| 17.78 | F | F | 1 | 0 | m,p | ![acetate O-R³] | H | Et | CH₂CF₃ |
| 17.79 | F | F | 1 | 0 | m,p | ![acetate O-R³] | H | Et | n-Prop |
| 17.80 | F | F | 1 | 0 | m,p | ![acetate O-R³] | H | Et | i-Prop |
| 17.81 | F | F | 1 | 0 | m,p | H | H | Et | — |
| 17.82 | F | F | 1 | 0 | o,m | ![acetate O-R³] | H | Me | CH₂CH₂OMe |
| 17.83 | F | F | 1 | 0 | o,m | ![ketone R³] | H | Me | i-Prop |
| 17.84 | F | F | 1 | 0 | o,m | ![amide NR⁴R⁵] | H | Me | — |
| 17.85 | F | F | 1 | 0 | o,m | ![ketone R³] | H | Me | CF₂Cl |
| 17.86 | F | F | 1 | 0 | o,m | CH₃ | H | Me | — |
| 17.87 | F | F | 1 | 0 | o,m | ![acetate OR³] | H | Me | CH₃ |
| 17.88 | F | F | 1 | 0 | o,m | ![acetate OR³] | H | Me | CH₂—CF₂—CHF₂ |
| 17.89 | F | F | 1 | 0 | o,m | ![thioester S-R⁶] | H | Me | — |

TABLE 17-continued
synthesized compounds
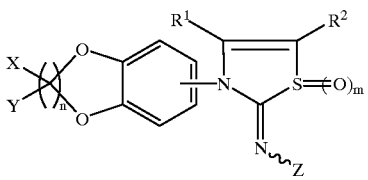
| | | | | | | | | | |
|---|---|---|---|---|---|---|---|---|---|
| 17.90 | F | F | 1 | 0 | o,m | 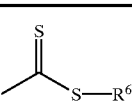 | H | Me | — |
| 17.91 | F | F | 1 | 0 | o,m |  | H | Et | $CF_2Cl$ |
| 17.92 | F | F | 1 | 0 | o,m |  | H | Et | $CF_2H$ |
| 17.93 | F | F | 1 | 0 | o,m |  | H | Et | $CF_3$ |
| 17.94 | F | F | 1 | 0 | o,m |  | H | Et | $C_2F_5$ |
| 17.95 | F | F | 1 | 0 | m,p | 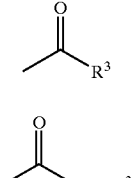 | H | Et | $CH_2CH_2F$ |
| 17.96 | F | F | 1 | 0 | m,p | 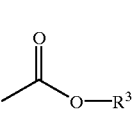 | H | Et | $CH_2CF_3$ |
| 17.97 | F | F | 1 | 0 | m,p | 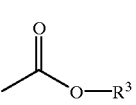 | H | Et | 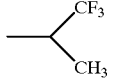 |
| 17.98 | F | F | 1 | 0 | m,p | 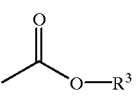 | H | Et | $CH_2-CF_2-CF_2H$ |
| 17.99 | F | F | 1 | 0 | o,m |  | H | Et | $CH_3$ |
| 17.100 | F | F | 1 | 0 | o,m | H | H | Et | — |
| 17.101 | F | F | 1 | 0 | o,m |  | H | $CH=CH_2$ | $CH_2Cl$ |
| 17.102 | F | F | 1 | 0 | o,m |  | H | $CH=CH_2$ | $CCl_3$ |

TABLE 17-continued
synthesized compounds
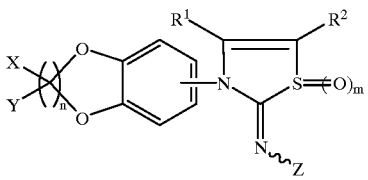
| No. | X | Y | n | m | pos | Z | R¹ | R² | R³ |
|---|---|---|---|---|---|---|---|---|---|
| 17.103 | F | F | 1 | 0 | o,m |  | H | CH=CH$_2$ | CHF$_2$ |
| 17.104 | F | F | 1 | 0 | o,m |  | H | CH=CH$_2$ | CH$_3$ |
| 17.105 | F | F | 1 | 0 | o,m | H | H | CH=CH$_2$ | — |
| 17.106 | H | H | 2 | 0 | m,p |  | H | Me | 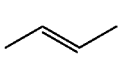 |
| 17.107 | H | H | 2 | 0 | m,p |  | H | Me | t-Bu |
| 17.108 | H | H | 2 | 0 | m,p |  | H | Me | i-Prop |
| 17.109 | H | H | 2 | 0 | m,p |  | H | Me | CH$_3$ |
| 17.110 | H | H | 2 | 0 | m,p |  | H | Me | CF$_3$ |
| 17.111 | H | H | 2 | 0 | m,p |  | H | Me | CHF$_2$ |
| 17.112 | H | H | 2 | 0 | m,p | 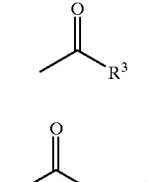 | H | Me | CH$_2$CH$_2$F |
| 17.113 | H | H | 2 | 0 | m,p | 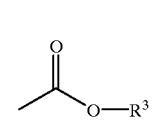 | H | Me | Me |
| 17.114 | H | H | 2 | 0 | m,p | 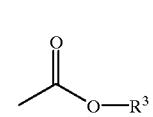 | H | Me | CH$_2$CF$_3$ |

TABLE 17-continued
synthesized compounds
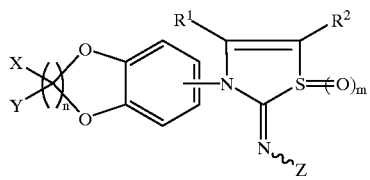
| | R¹ | R² | n | m | | Z | R¹ | R² | |
|---|---|---|---|---|---|---|---|---|---|
| 17.115 | H | H | 2 | 0 | m,p | 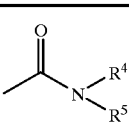 | H | Me | — |
| 17.116 | H | H | 2 | 0 | m,p | 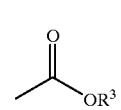 | H | Me | n-Prop |
| 17.117 | H | H | 2 | 0 | m,p | 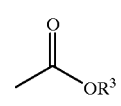 | H | Me | i-Prop |
| 17.118 | H | H | 2 | 0 | m,p | 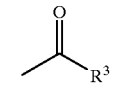 | H | Me | CF₂Cl |
| 17.119 | H | H | 2 | 0 | m,p | 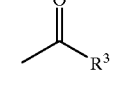 | H | Me | C₂F₅ |
| 17.120 | H | H | 2 | 0 | o,m | 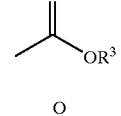 | H | Me | Ph |
| 17.121 | H | H | 2 | 0 | m,p | 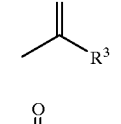 | H | Me | CCl₂—CH₃ |
| 17.122 | H | H | 2 | 0 | m,p | 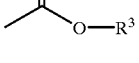 | H | Me | i-Bu |
| 17.123 | H | H | 2 | 0 | m,p | 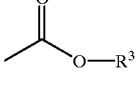 | H | Me | s-Bu |
| 17.124 | H | H | 2 | 0 | m,p | 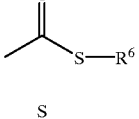 | H | Me | — |
| 17.125 | H | H | 2 | 0 | m,p | 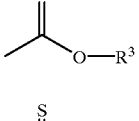 | H | Me | Ph |
| 17.126 | H | H | 2 | 0 | m,p | 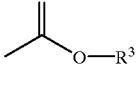 | H | Me | 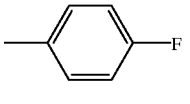 |

TABLE 17-continued
synthesized compounds
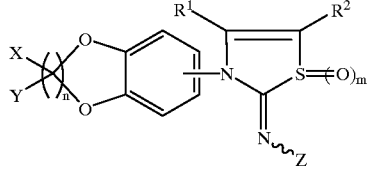
| No. | X | Y | n | m | pos. | group | R¹ | R² | Z |
|---|---|---|---|---|---|---|---|---|---|
| 17.127 | H | H | 2 | 0 | m,p | 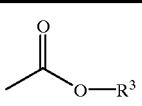 | H | Me | CH₂CF₂CF₂H |
| 17.128 | H | H | 2 | 0 | m,p |  | H | Me |  |
| 17.129 | H | H | 2 | 0 | m,p | 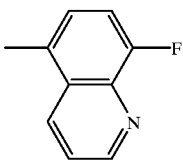 | H | Me | CH₂CH₂OMe |
| 17.130 | H | H | 2 | 0 | m,p | 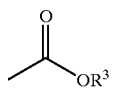 | H | Me | t-Bu |
| 17.131 | H | H | 2 | 0 | m,p | 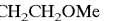 | H | Me | 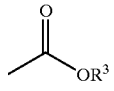 |
| 17.132 | H | H | 2 | 0 | m,p |  | H | Me |  |
| 17.133 | H | H | 2 | 0 | m,p | 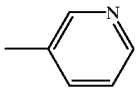 | H | Me |  |
| 17.134 | H | H | 2 | 0 | m,p | 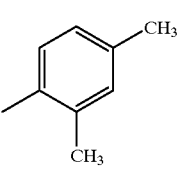 | H | Me | — |
| 17.135 | H | H | 2 | 0 | m,p |  | H | Me | — |
| 17.136 | F | F | 2 | 0 | m,p | H | H | Me | — |
| 17.137 | F | F | 2 | 0 | m,p | 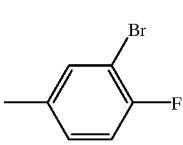 | H | Me | CH₃ |

TABLE 17-continued
synthesized compounds
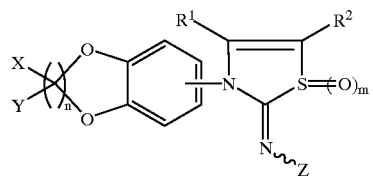
| No. | R¹ | R² | n | m | | R³ | R¹ | R² | |
|---|---|---|---|---|---|---|---|---|---|
| 17.138 | F | F | 2 | 0 | m,p | (C(=O)R³) | H | Me | CHF₂ |
| 17.139 | F | F | 2 | 0 | m,p | (C(=O)R³) | H | Me | CF₃ |
| 17.140 | F | F | 2 | 0 | m,p | (C(=O)R³) | H | Me | C₂F₅ |
| 17.141 | F | F | 2 | 0 | m,p | (C(=O)OR³) | H | Me | CH₂—CH₂F |
| 17.142 | F | F | 2 | 0 | m,p | (C(=O)OR³) | H | Me | CH₂—CF₃ |
| 17.143 | F | F | 2 | 0 | m,p | (C(=O)OR³) | H | Me | CH₂—CF₂—CF₂H |
| 17.144 | F | F | 2 | 0 | m,p | (C(=O)OR³) | H | Me | CH(CF₃)(CH₃) |
| No. | R⁴ | R⁵ | R⁶ | Data |
|---|---|---|---|---|
| 17.1 | — | — | — | 220° C. Decomp. |
| 17.2 | — | — | — | 203–205° C. |
| 17.3 | — | — | — | 179–180° C. |
| 17.4 | — | — | — | 175–177° C. |
| 17.5 | — | — | — | 106–107° C. |
| 17.6 | — | — | — | 131–134° C. |
| 17.7 | — | — | — | 165–169° C. |
| 17.8 | — | — | — | 147–148° C. |
| 17.9 | — | — | — | 171–174° C. |
| 17.10 | — | — | — | 146–148° C. |
| 17.11 | — | — | — | 211–213° C. |
| 17.12 | — | — | — | 151–153° C. |
| 17.13 | — | — | — | ¹H; DMSO; 0.85(t, 3H) 1.55(m, 2H) 2.25(s, 3H) 3.93(t, 2H) 7.25(s, 1H) 7.35(d, 1H) 7.55(d, 1H) 7.72(s, 1H) |
| 17.14 | — | — | — | 129–131° C. |
| 17.15 | — | — | — | 81–84° C. |
| 17.16 | — | — | — | 134–135° C. |

TABLE 17-continued
synthesized compounds
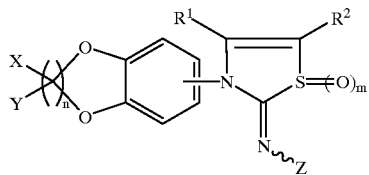
| | R¹ | R² | Z | |
|---|---|---|---|---|
| 17.17 | — | — | — | 81° C. |
| 17.18 | — | — | — | ¹H; CDCl₃; 1.50(t, 9H) 2.25(s, 3H) 6.65(s, 1H) 7.12(m, 2H) 7.32(s, 1H) |
| 17.19 | — | — | — | 72–74° C. |
| 17.20 | — | — | — | 78–79° C. |
| 17.21 | — | — | — | 62–64° C. |
| 17.22 | — | — | — | 102–104° C. |
| 17.23 | — | — | — | ¹H; CDCl₃; 1.0–2.0(m, 10H) 2.25(s, 3H) 4.65(m, 1H) 6.60(s, 1H) 7.18(m, 2H) 7.30(s, 1H) |
| 17.24 | — | — | — | ¹H; CDCl₃; 1.95(n, 3H) 2.25(s, 3H) 4.72(d, 2H) 6.70(s, 1H) 7.12(m, 2H) 7.30(s, 1H) |
| 17.25 | — | — | — | 82–84° C. |
| 17.26 | — | — | — | 113–115° C. |
| 17.27 | — | — | — | 104–105° C. |
| 17.28 | — | — | — | 172–135° C. |
| 17.29 | — | — | — | |
| 17.30 | — | — | — | ¹H; CDCl₃; 1.35(d, 3H) 2.25(s, 3H) 3.40–3.70(m, 2H) 5.50(m, 1H) 6.65(s, 1H) 7.22(m, 2H) 7.28(s, 1H) |
| 17.31 | — | — | — | ¹H; CDCl₃; 0.85(t, 2H) 2.25(s, 3H) 3.57(t, 2H) 6.42(s, 1H) 7.10(m, 2H) 7.45(s, 1H) |
| 17.32 | — | — | — | 151–153° C. |
| 17.33 | — | — | — | 161–163° C. |
| 17.34 | — | — | — | 173–176° C. |
| 17.35 | — | — | — | 134–137° C. |
| 17.36 | — | — | — | ¹H; CDCl₃; 2.25(s, 3H) 6.65(s, 1H) 7.0–8.0 (m, 10H) |
| 17.37 | — | — | — | 96–98° C. |
| 17.38 | — | — | — | 102–104° C. |
| 17.39 | — | — | 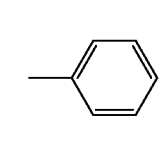 | 120–140° C. |
| 17.40 | — | — | — | 172–173° C. |
| 17.41 | — | — | — | 176–184° C. |
| 17.42 | — | — | — | 195–198° C. |

TABLE 17-continued
synthesized compounds
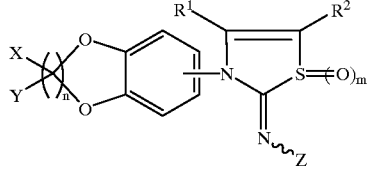
| | R¹ | R² | Z | |
|---|---|---|---|---|
| 17.43 | — | — | 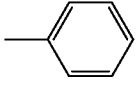 | ¹H; CDCl₃; 2.30(s, 3H) 6.85(m, 3H) 7.15(m, 2H) 7.25(m, 3H) |
| 17.44 | — | — | — | 90–92° C. |
| 17.45 | — | — | — | 124–135° C. |
| 17.46 | CH₃ | CH₃ | — | 149–151° C. |
| 17.47 | Et | Et | — | |
| 17.48 | — | — | — | 191–192° C. |
| 17.49 | — | — | — | 235–239° C. |
| 17.50 | — | — | — | 185–190° C. |
| 17.51 | — | — | — | 167–173° C. |
| 17.52 | — | — | — | 138–141° C. |
| 17.53 | — | — | — | 92–98° C. |
| 17.54 | — | — | — | 119–121° C. |
| 17.55 | — | — | — | 137–141° C. |
| 17.56 | Me | Me | — | 149–151° C. |
| 17.57 | — | — | — | 141–146° C. |
| 17.58 | — | — | — | 133–136° C. |
| 17.59 | — | — | — | 144–147° C. |
| 17.60 | — | — | — | 111–113° C. |
| 17.61 | — | — | — | 133–135° C. |
| 17.62 | — | — | — | 141–144° C. |
| 17.63 | — | — | — | 120–123° C. |
| 17.64 | — | — | — | 173–175° C. |
| 17.65 | — | — | — | 163–166° C. |
| 17.66 | — | — | — | 163–166° C. |
| 17.67 | — | — | — | 119–121° C. |
| 17.68 | — | — | — | |
| 17.69 | — | — | — | 154–156° C. |
| 17.70 | — | — | — | 98–100° C. |
| 17.71 | — | — | — | ¹H, CDCl₃: 2.15(s, 3H); 2.35(s, 3H); 5.9(s, 1H); 6.85(dd, 1H); 6.90(d, 1H); 7.05(d, 1H) |
| 17.72 | — | — | — | 81–84° C. |
| 17.73 | CH₃ | 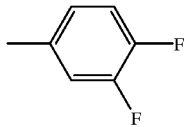 | — | 101–102° C. |
| 17.74 | — |  | — | ¹H, CDCl₃; 2.15(s, 3H): 3.6(m, br, 8H); 6.58(s, 1H); 7.08(m, 3H) |
| 17.75 | — | — | — | 100–105° C. |
| 17.76 | — | — | — | 112–114° C. |
| 17.77 | — | — | — | ¹H, CDCl₃: 1.28(t, 3H); 2.72(q, 2H); 4.2–4.8(m, 4H); 6.7(s, 1H); 7.1(m, 2H); 7.28(d, 1H) |
| 17.78 | — | — | — | ¹H, CDCl₃: |

TABLE 17-continued
synthesized compounds
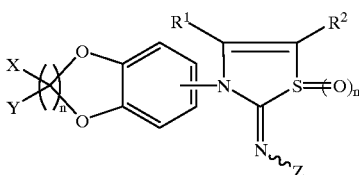
| No. | R¹ | R² | Z | mp / ¹H NMR |
|---|---|---|---|---|
| | | | | 1.30(t, 3H); 2.70(q, 2H); 4.55(q, 2H); 6.70(s, 1H); 7.10–7.20(m, 2H); 7.18(s, 1H) |
| 17.79 | — | — | — | ¹H, CDCl₃: 0.92(t, 3H); 1.14(t, 3H); 1.60–180(m, 2H); 2.62(q, 2H); 4.10(t, 2H); 6.83(s, 1H); 7.10(m, 2H); 7.29(d, 1H) |
| 17.80 | — | — | — | ¹H, CDCl₃: 1.22–1.33(m, 9H); 2.65(q, 2H); 5.00(q, 1H); 6.65(s, 1H); 7.15(m, 2H); 7.32(d, 1H) |
| 17.81 | — | — | — | 200–202° C. |
| 17.82 | — | — | — | 125–127° C. |
| 17.83 | — | — | — | 129–131° C. |
| 17.84 | CH₃ | 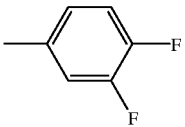 | — | 101–103° C. |
| 17.85 | — | — | — | 103–106° C. |
| 17.86 | — | — | — | ¹H, CDCl₃: 2.12(s, 3H); 2.34(s, 3H); 6.08(s, 1H); 6.85(d, 1H); 7.02(d, 1H); 7.10(dd, 1H) |
| 17.87 | — | — | — | 160°163° C. |
| 17.88 | — | — | — | 112–114° C. |
| 17.89 | — | — | Ph | 151° C. |
| 17.90 | — | — | Ph | 181–183° C. |
| 17.91 | — | — | — | 111–113° C. |
| 17.92 | — | — | — | 111–114° C. |
| 17.93 | — | — | — | 102–104° C. |
| 17.94 | — | — | — | 101–103° C. |
| 17.95 | — | — | — | 152–154° C. |
| 17.96 | — | — | — | 106–110° C. |
| 17.97 | — | — | — | 115–117° C. |
| 17.98 | — | — | — | 92–94° C. |
| 17.99 | — | — | — | 110–113° C. |
| 17.100 | — | — | — | 210–220° C. |
| 17.101 | — | — | — | 146–148° C. |
| 17.102 | — | — | — | 146–149° C. |
| 17.103 | — | — | — | 140–147° C. |
| 17.104 | — | — | — | 145–148° C. |
| 17.105 | — | — | — | ¹H, DMSO: 5.41(d, 1H); 5.55(d, 1H); 6.80(dd, 1H); 7.40–7.60(m, 2H); 7.75(dd, 1H) |

TABLE 17-continued
synthesized compounds
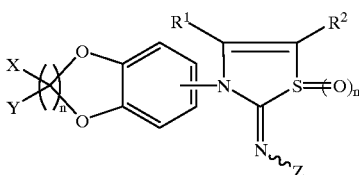
| | R¹ | R² | Z | |
|---|---|---|---|---|
| 17.106 | — | — | — | 167–170° C. |
| 17.107 | — | — | — | 144–147° C. |
| 17.108 | — | — | — | ¹H, CDCl₃: 1.16(d, 6H); 2.30(s, 3H); 2.70(m, 1H); 4.30(s, 4H); 6.75(s, 1H); 7.00(m, 2H); 7.08(d, 1H) |
| 17.109 | — | — | — | 147–150° C. |
| 17.110 | — | — | — | 166–169° C. |
| 17.111 | — | — | — | 159–161° C. |
| 17.112 | — | — | — | 167–170° C. |
| 17.113 | — | — | — | 185–189° C. |
| 17.114 | — | — | — | 160–162° C. |
| 17.115 | |  | — | 134–136° C. |
| 17.116 | — | — | — | 150–152° C. |
| 17.117 | — | — | — | 197–200° C. |
| 17.118 | — | — | — | 108–114° C. |
| 17.119 | — | — | — | 160–162° C. |
| 17.120 | — | — | — | 140–141° C. |
| 17.121 | — | — | — | 175–176° C. |
| 17.122 | — | — | — | 126–127° C. |
| 17.123 | — | — | — | 117–121° C. |
| 17.124 | — | — | Ph | 159–162° C. |
| 17.125 | — | — | — | 175–177° C. |
| 17.126 | — | — | — | 215–217° C. |
| 17.127 | — | — | — | 113–114° C. |
| 17.128 | — | — | — | 208–213° C. |
| 17.129 | — | — | — | 115–117° C. |
| 17.130 | — | — | — | 196–199° C. |
| 17.131 | — | — | — | 184–185° C. |
| 17.132 | — | — | — | 136–139° C. |
| 17.133 | — | — | — | 224–226° C. |
| 17.134 | Ph | Ph | — | 200–210° C. |
| 17.135 | Me | 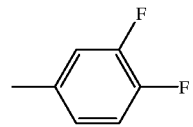 | — | 160–167° C. |
| 17.136 | — | — | — | 248–250° C. |
| 17.137 | — | — | — | 155–157° C. |
| 17.138 | — | — | — | 115–118° C. |
| 17.139 | — | — | — | 98–100° C. |
| 17.140 | — | — | — | 95–97° C. |
| 17.141 | — | — | — | 114–115° C. |
| 17.142 | — | — | — | ¹H, CDCl₃: 2.35(s, 3H); 4.55(q, 2H); 6.65(s, 1H); 7.22–7.35(m, 3H) |
| 17.143 | — | — | — | 116–119° C. |
| 17.144 | — | — | — | 104–111° C. |

The compounds I and their agriculturally useful salts are suitable, both in the form of isomer mixtures and in the form of the pure isomers, as herbicides. The herbicidal compositions comprising I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the compounds I, or compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris spec. altissima, Beta vulgaris spec. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, medicago sativa, Musa spec., Nicotiana tabacum(N.rustica), Olea europaea, Oryza sativa, Phaseolus lunatus, Phaseolus vulgaris, Picea abies, Pinus spec., Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera* and *Zea mays.*

In addition, the compounds I may also be used in crops which tolerate the action of herbicides owing to breeding, including genetic engineering methods.

The active compounds or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into as little contact as possible, if any, with the leaves of the sensitive crop plants, while the active compounds reach the leaves of undesirable plants growing underneath, or the bare soil surface (post-directed, lay-by).

The compounds I, or the herbicidal compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for spreading, or granules, by means of spraying, atomizing, dusting, spreading or watering. The use forms depend on the intended aims; in any case, they should guarantee the finest possible distribution of the active compounds according to the invention.

Suitable inert auxiliaries are essentially: mineral oil fractions of medium to high boiling point, such as kerosene and diesel oil, furthermore coal tar oils and oils of vegetable or animal origin, aliphatic, cyclic and aromatic hydrocarbons, eg. paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the thiazolimine derivatives, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ether, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding the active compounds together with a solid carrier.

Granules, eg. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise from 0.001 to 98% by weight, preferably 0.01 to 95% by weight of at least one active compound. The active compounds are employed in a purity of from 90% to 100%, preferably 95% to 100% (according to NMR spectrum).

The formulation examples which follow illustrate the preparation of the compounds I according to the invention:

I. 20 parts by weight of the compound No. 13.13 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of the compound No. 13.13 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of the active compound No. 13.13 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of the active compound No. 13.13 are mixed thoroughly with 3 parts by weight of the sodium salt of diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of the active compound No. 13.13 are mixed with 97 parts by weight of finely divided kaolin. This gives a dust which comprises 3% by weight of active compound.

VI. 20 parts by weight of the active compound No. 13.13 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. 13.13 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound No. 13.13 is dissolved in a mixture composed of 80 parts by weight of cyclohexanone and 20 parts by weight of Wettol® EM 31 (nonionic emulsifier based on ethoxylated castor oil). This gives a stable emulsion concentrate.

To widen the spectrum of action and to achieve synergistic effects, the thiazolimine derivatives may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acid and its derivatives, benzoic acid and its derivatives, benzothiadiazinones, 2-aroyl-1,3-cyclohexanediones, hetaryl aryl ketones, benzylisoxazolidinones, meta-$CF_3$-phenyl derivatives, carbamates, quinolinecarboxylic acid and its derivates, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Nonphytotoxic oils and oil concentrates may also be added.

The rates of application of active compound are from 0.001 to 3.0, preferably 0.01 to 1.0, kg/ha of active substance (a.s.), depending on the control target, the season, the target plants and the growth stage.

Use Examples

The herbicidal activity of the thiazolimine derivatives of the formula I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active compounds, which had been suspended or emulsified in water, were applied directly after sowing by means of finely distributing nozzles. The containers were irrigated gently to promote germination and growth and subsequently covered with translucent plastic hoods until the plants had rooted. This cover causes uniform germination of the test plants, unless this was adversely affected by the active compounds. The rate of application for the pre-emergence treatment was 0.5 or 0.25 kg/ha of a.s.

For the post-emergence treatment, the test plants were first grown to a plant height of 3 to 15 cm, depending on the plant habit, and only then treated with the active compounds which had been suspended or emulsified in water. The test plants for this purpose were either sown directly and grown in the same containers, or they were first grown separately as seedlings and transplanted into the test containers a few days prior to treatment.

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage, or normal course of growth.

The plants used in the greenhouse experiments were from the following species:

| Scientific Name | Common Name | Abbreviation |
|---|---|---|
| *Glycine max* | soybeans | GLXMA |
| *Gossypium hirsutum* | cotton | GOSHI |
| *Triticum aestivum* | summer wheat | TRZAS |
| *Amaranthus retroflexus* | redroot pigweed | AMARE |
| *Eleusine indica* | wiregrass | ELEIN |

TABLE 14

Selective herbicidal activity when applied pre-emergence (greenhouse)

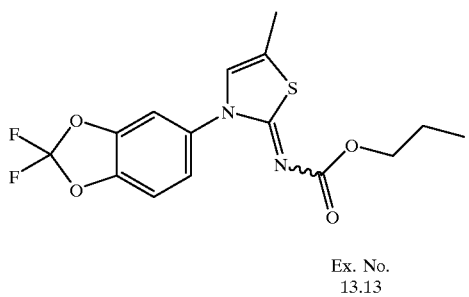

Ex. No. 13.13

| Application rate (kg/ha a. s.) | 0.5 | 0.25 |
|---|---|---|
| Test plants | | |
| GLXMA | 0 | 0 |
| GOSHI | 0 | 0 |
| TRZAS | 0 | 0 |
| ELEIN | 85 | 85 |
| SETFA | 98 | 95 |
| SETVI | 100 | 98 |

TABLE 15

Selective herbicidal activity when applied pre-emergence (greenhouse)

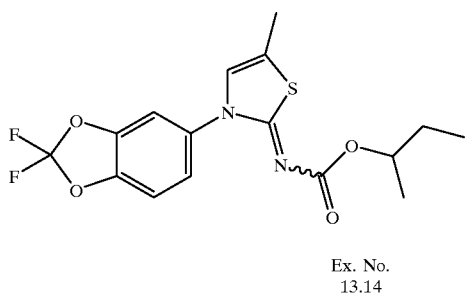

Ex. No. 13.14

| Application rate (kg/ha a. s.) | 0.5 | 0.25 |
|---|---|---|
| Test plants | | |
| GLXMA | 0 | 0 |
| GOSHI | 0 | 0 |
| AMARE | 100 | 90 |
| SETFA | 100 | 98 |
| SETVI | 100 | 100 |
| VERSS | 90 | 90 |

-continued

| Scientific Name | Common Name | Abbreviation |
|---|---|---|
| *Setaria faberii* | giant foxtail | SETFA |
| *Setaria viridis* | green foxtail | SETVI |
| Veronica spp. | speedwell | VERSS |

We claim:
1. A thiazolimine derivative of the formula I

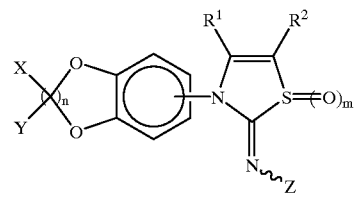

where:
X and Y independently of one another are each hydrogen or halogen;
Z is hydrogen; $C_1$–$C_8$-alkyl, $C_2$–$C_8$-alkenyl, $C_2$–$C_8$-alkynyl, $C_1$–$C_8$-alkoxy, $C_1$–$C_8$-alkylthio, it being possible for these groups to be substituted by one to five halogens or $C_1$–$C_4$-alkoxy; or one of the groups below:

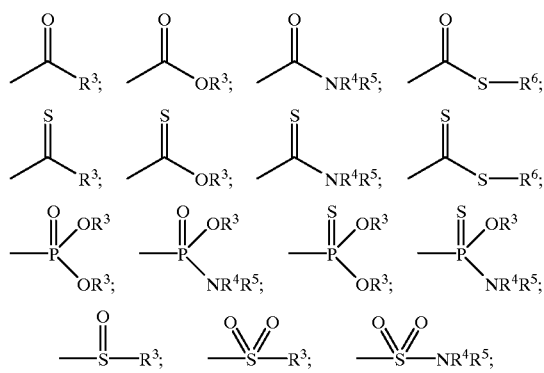

$R^1$ is hydrogen;
$R^2$ is hydrogen, halogen; $C_1$–$C_4$-alkyl, $C_2$–$C_4$-alkenyl, $C_2$–$C_4$-alkynyl, it being possible for these groups to be substituted by one to five halogens or by $C_1$–$C_4$-alkoxy;
$R^3$ is hydrogen; $C_1$–$C_8$-alkyl, $C_2$–$C_8$-alkenyl, $C_2$–$C_8$-alkynyl, $C_2$–$C8$-alkylcarbonyl, $C_3$–$C_8$-alkenylcarbonyl, $C_3$–$C_8$-alkynylcarbonyl, it being possible for these groups to be substituted by one to eight halogens or by $C_1$–$C_4$-alkoxy; $C_3$–$C_7$-cycloalkyl, $C_3$–$C_7$-cycloalkenyl, it being possible for these groups to be substituted by one to eight halogen atoms, $C_1$–$C_4$-alkoxy, $C_1$–$C_4$-alkyl or $C_1$–$C_4$-haloalkyl; aryl, hetaryl, benzyl, it being possible for these groups to be substituted by $C_1$–$C_4$-alkyl, $C_1$–$C_4$-haloalkyl, $C_1$–$C_4$-alkoxy, $C_1$–$C_4$-haloalkoxy, halogen, cyano, or nitro;
$R^4$ and $R^5$ are each hydrogen; $C_1$–$C_6$-alkyl, $C_2$–$C_6$-alkenyl, $C_2$–$C_6$-alkynyl, it being possible for these groups to be substituted by one to four halogens or by $C_1$–$C_4$-alkoxy; $C_3$–$C_7$-cycloalkyl, $C_3$–$C_7$-cycloalkenyl, which may be substituted by one to four halogens or by $C_1$–$C_4$-alkyl, $C_1$–$C_4$-haloalkyl, $C_1$–$C_4$-alkoxy, $C_1$–$C_4$-haloalkoxy; aryl, hetaryl, it being possible for these groups to be substituted by $C_1$–$C_4$-alkyl, $C_1$–$C_4$-alkoxy, $C_1$–$C_4$-haloalkyl, $C_1$–$C_4$-haloalkoxy, halogen, nitro or cyano;
$R^4$ and $R^5$ together form a 3- to 7-membered heterocycle which may carry a further hetero atom from the group consisting of N, O and S, may contain at least one double bond and may be substituted by $C_1$–$C_4$-alkyl, $C_1$–$C_4$-haloalkyl, $C_1$–$C_4$-alkoxy, $C_1$–$C_4$-haloalkoxy, halogen, nitro or cyano;

$R^6$ is hydrogen; $C_1$–$C_6$-alkyl, $C_2$–$C_6$-alkenyl, $C_2$–$C_6$-alkynyl, it being possible for these groups to be substituted by one to four halogens or by alkoxy; $C_3$–$C_7$-cycloalkyl, $C_3$–$C_7$-cycloalkenyl, which may be substituted by one to four halogen atoms or by $C_1$–$C_4$-alkyl, $C_1$–$C_4$-haloalkyl, $C_1$–$C_4$-alkoxy, haloalkoxy; aryl, hetaryl, it being possible for these groups to be substituted by $C_1$–$C_4$-alkyl $C_1$–$C_4$-haloalkyl, $C_1$–$C_4$-alkoxy, $C_1$–$C_4$-haloalkoxy, halogen, nitro or cyano;

n is 1 or 2;

m is 0, 1 or 2 and agriculturally useful salts of the compounds I.

2. A thiazolimine derivative of the formula I as claimed in claim 1 where n=1.

3. A thiazolimine of the formula I as claimed claim 1 where n=2.

4. A thiazolimine derivative of the formula I as claimed in claim 1 where the thiazolimine substituent is attached to the benzene ring ortho to one of the oxygen atoms of the heterocycle.

5. A thiazolimine derivative of the formula I as claimed in claim 1 where the thiazolimine substituent is attached to the benzene ring meta to one and para to the other oxygen atom of the heterocycle.

6. A thiazolimine derivative of the formula I as claimed in claim 1 where m=0.

7. A thiazolimine derivative of the formula I as claimed in claim 1 where m=1.

8. A thiazolimine derivative of the formula I as claimed in claim 1 where m=2.

9. A process for preparing a thiazolimine derivative of the formula I as claimed in claim 1, which comprises reacting anilines of the formula II with propargyl derivatives of the formula III

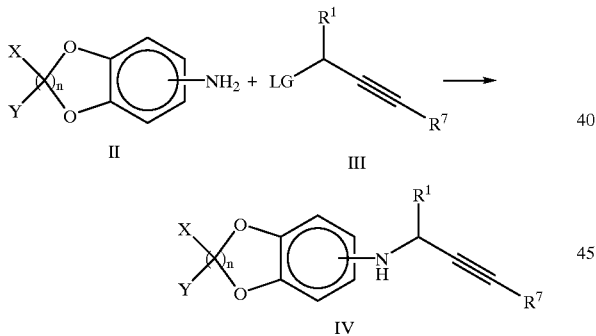

where LG is a nucleophilically replaceable leaving group and the substituent $R^7$ has the following meaning:

$R^7$ is hydrogen, halogen; $C_1$–$C_3$-alkyl, $C_2$–$C_3$-alkenyl, $C_2$–$C_3$-alkynyl, it being possible for these groups to be substituted by one to five halogens or by $C_1$–$C_4$-alkoxy; reacting the resulting aniline derivative of the formula IV with KSCN and acetyl chloride and converting them with a base or an acid into the N-acetylthiazolimine derivatives of the formula VIII

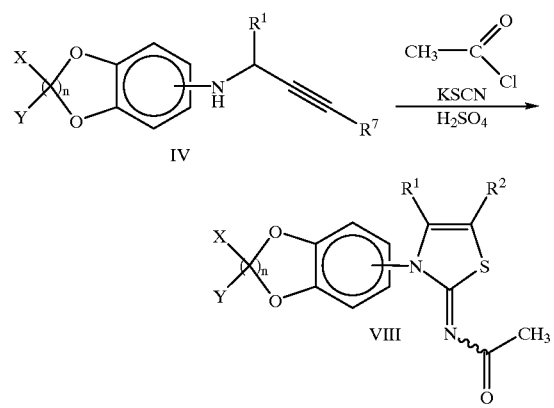

which are, by acid treatment, converted into their salts which are then reacted with the compounds of the formula X to give the thiazolimine derivatives of the formula I

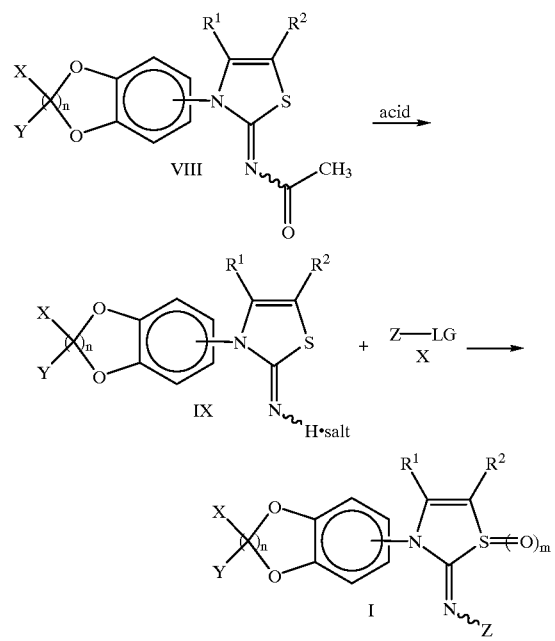

where LG is a nucleophilically replaceable leaving group.

10. A herbicidal composition comprising a herbicidally effective amount of at least one compound of the formula I as claimed in claim 1 and at least one inert liquid and/or solid carrier and, if desired, at least one adjuvant.

11. A method for controlling undesirable vegetation, which comprises allowing a herbicidally effective amount of a compound of the formula I as claimed in claim 1 to act on plants, their habitat or their seeds.

* * * * *

UNITED STATES PATENT AND TRADEMARK OFFICE
CERTIFICATE OF CORRECTION

PATENT NO.: 6,165,943

DATED: December 26, 2000

INVENTOR(S): MAYER et al.

It is certified that error appears in the above-identified patent and that said Letters Patent is hereby corrected as shown below:

Col. 78, claim 1, line 41, "$C_1$-$C_8$-alkyl" should be --$C_1$-$C_8$-alkyl--.

Col. 78, claim 1, line 42, "$C_2$-C8-alkylcarbonyl" should be --$C_2$-$C_8$-alkylcarbonyl--

Col. 78, claim 1, line 52, "$C_1$-$C_6$-alkyl" should be --$C_1$-$C_6$-alkyl--.

Col. 78, claim 1, lines 58 and 60, "$C_1$-$C_4$-haloalkoxy" should be --$C_1$-$C_4$-haloalkoxy--.

Signed and Sealed this

First Day of May, 2001

*Attest:*

NICHOLAS P. GODICI

*Attesting Officer*  *Acting Director of the United States Patent and Trademark Office*